United States Patent
Nelson et al.

(10) Patent No.: US 8,752,552 B2
(45) Date of Patent: Jun. 17, 2014

(54) DEVICES, SYSTEMS, AND METHODS TO FIXATE TISSUE WITHIN THE REGIONS OF BODY, SUCH AS THE PHARYNGEAL CONDUIT

(75) Inventors: Lionel M. Nelson, Los Altos, CA (US); Eric N. Doelling, Sunnyvale, CA (US); Ronald G. Lax, Tarpon Springs, FL (US); Jinfang Liu, Lancaster, PA (US); Ryan P. Boucher, San Francisco, CA (US); Allan R. Will, Atherton, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 12/148,175

(22) Filed: Apr. 17, 2008

(65) Prior Publication Data

US 2008/0221684 A1   Sep. 11, 2008

Related U.S. Application Data

(60) Division of application No. 10/718,254, filed on Nov. 20, 2003, now Pat. No. 7,360,542, which is a continuation-in-part of application No. 10/656,861, filed on Sep. 6, 2003, now Pat. No. 7,188,627, and a continuation-in-part of application No. 10/236,455, filed on Sep. 6, 2002, now Pat. No. 7,216,648.

(60) Provisional application No. 60/441,639, filed on Jan. 22, 2003, provisional application No. 60/456,164, filed on Mar. 20, 2003.

(51) Int. Cl.
- A61F 5/37      (2006.01)
- A61F 13/00     (2006.01)
- A61B 19/00     (2006.01)
- A61B 17/08     (2006.01)
- A61B 1/00      (2006.01)

(52) U.S. Cl.
USPC ........... 128/848; 128/846; 128/898; 602/902; 606/213; 623/14.11; 623/23.72

(58) Field of Classification Search
USPC ................. 128/848, 831, 842, 898; 602/902; 606/213; 623/14.11, 23.72
See application file for complete search history.

(56) References Cited

U.S. PATENT DOCUMENTS

| | | | | |
|---|---|---|---|---|
| 3,991,743 A | * | 11/1976 | Bucalo | 128/843 |
| 4,304,227 A | | 12/1981 | Samelson | |
| 4,920,982 A | * | 5/1990 | Goldstein | 128/842 |
| 4,978,323 A | | 12/1990 | Freedman | |
| 5,019,372 A | | 5/1991 | Folkman et al. | |
| 5,176,618 A | | 1/1993 | Freedman | |
| 5,220,918 A | | 6/1993 | Heide et al. | |
| 5,373,859 A | | 12/1994 | Forney | |
| 5,465,734 A | | 11/1995 | Alvarez et al. | |
| 5,649,540 A | | 7/1997 | Alvarez et al. | |
| 5,792,067 A | | 8/1998 | Karell | |
| RE36,120 E | | 3/1999 | Karell | |
| 5,979,456 A | | 11/1999 | Magovern | |
| 5,988,171 A | | 11/1999 | Sohn | |
| 6,231,496 B1 | | 5/2001 | Wilk | |
| 6,244,865 B1 | | 6/2001 | Nelson et al. | |
| 6,250,307 B1 | | 6/2001 | Conrad et al. | |

(Continued)

*Primary Examiner* — Patricia Bianco
*Assistant Examiner* — Brandon L Jackson

(57) ABSTRACT

Devices, systems and methods develop static and/or kinetic and/or pressure forces to fixate or brace tissue in targeted pharyngeal structures and individual anatomic components within the pharyngeal conduit.

12 Claims, 22 Drawing Sheets

(56) References Cited

U.S. PATENT DOCUMENTS

| | | |
|---|---|---|
| 6,390,096 B1 | 5/2002 | Conrad et al. |
| 6,401,717 B1 | 6/2002 | Conrad et al. |
| 6,408,851 B1 | 6/2002 | Karell |
| 6,415,796 B1 | 7/2002 | Conrad et al. |
| 6,431,174 B1 * | 8/2002 | Knudson et al. ............... 128/898 |
| 6,450,169 B1 | 9/2002 | Conrad et al. |
| 6,490,885 B1 | 12/2002 | Wilkinson |
| 6,523,541 B2 | 2/2003 | Knudson |
| 6,636,767 B1 | 10/2003 | Knudson et al. |
| 6,742,524 B2 | 6/2004 | Knudson et al. |
| 6,955,172 B2 | 10/2005 | Nelson et al. |
| 7,073,505 B2 | 7/2006 | Nelson et al. |
| 7,077,143 B2 | 7/2006 | Knudson et al. |
| 7,077,144 B2 | 7/2006 | Knudson et al. |
| 2001/0047805 A1 | 12/2001 | Scarberry et al. |
| 2004/0112390 A1 | 6/2004 | Brooks et al. |
| 2005/0092332 A1 | 5/2005 | Conrad et al. |

* cited by examiner

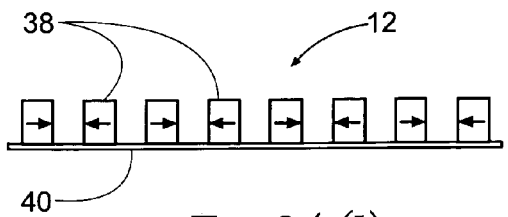
*Fig. 8A(1)*
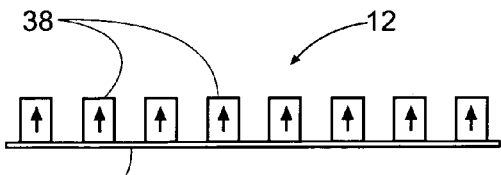
*Fig. 8A(2)*
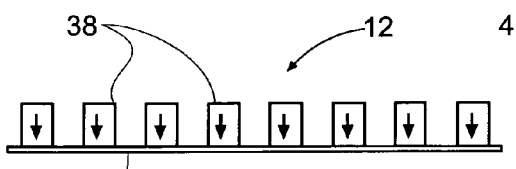
*Fig. 8A(3)*
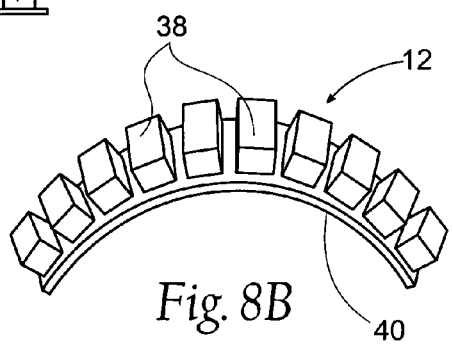
*Fig. 8B*
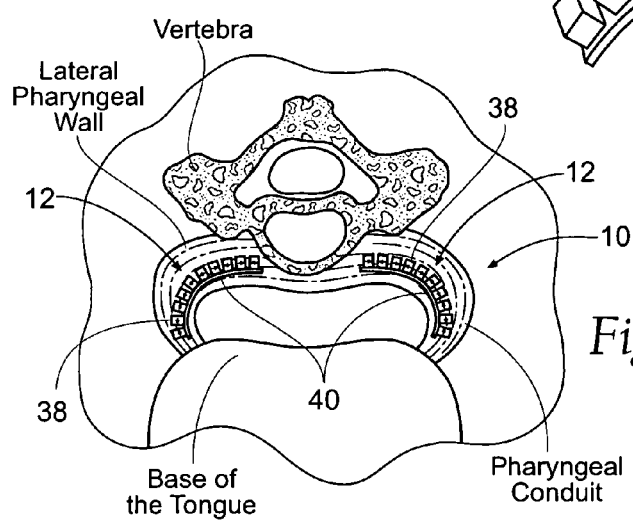
*Fig. 8C*
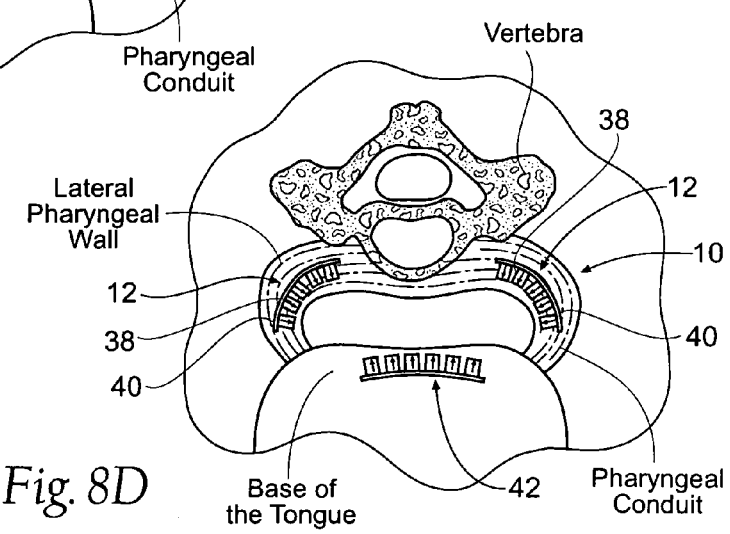
*Fig. 8D*

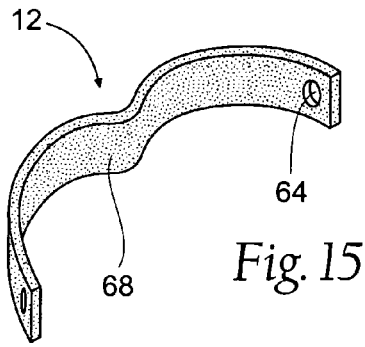
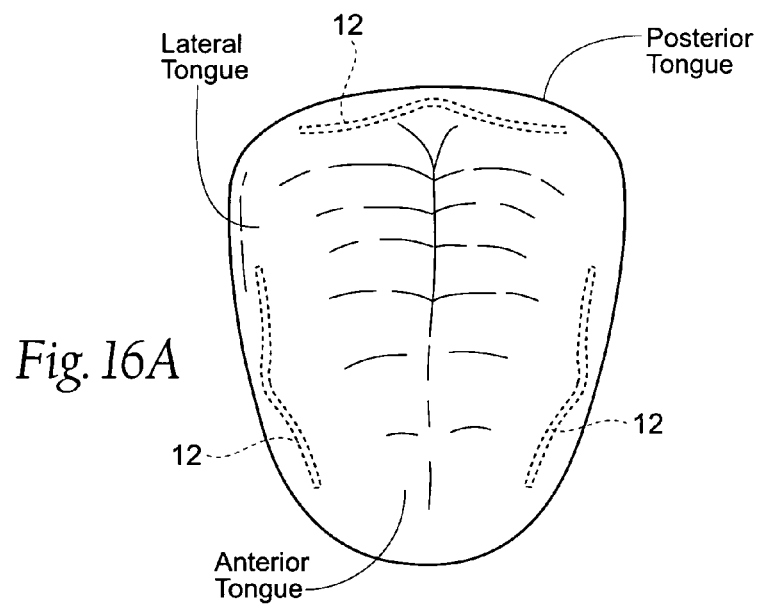
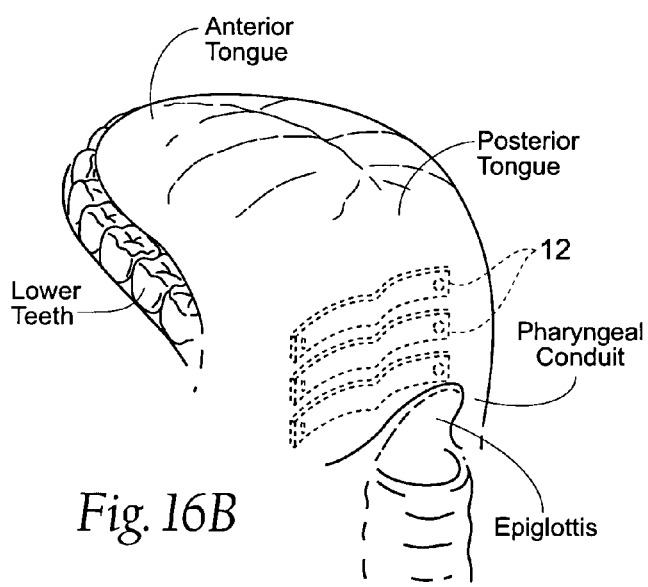

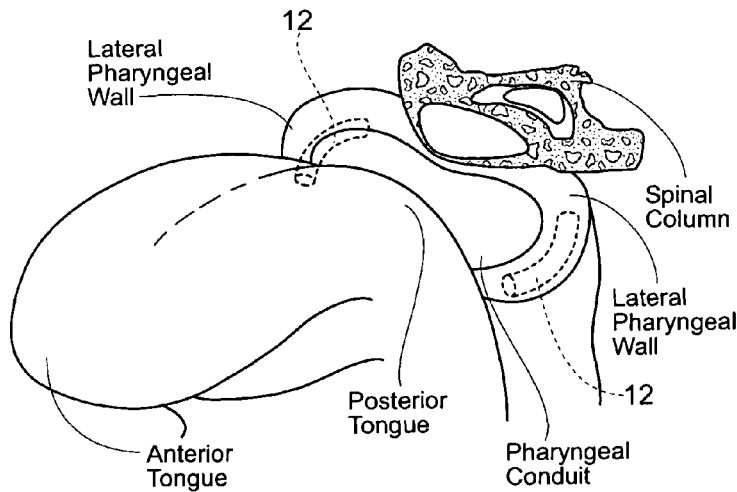
Fig. 17A
Fig. 17B
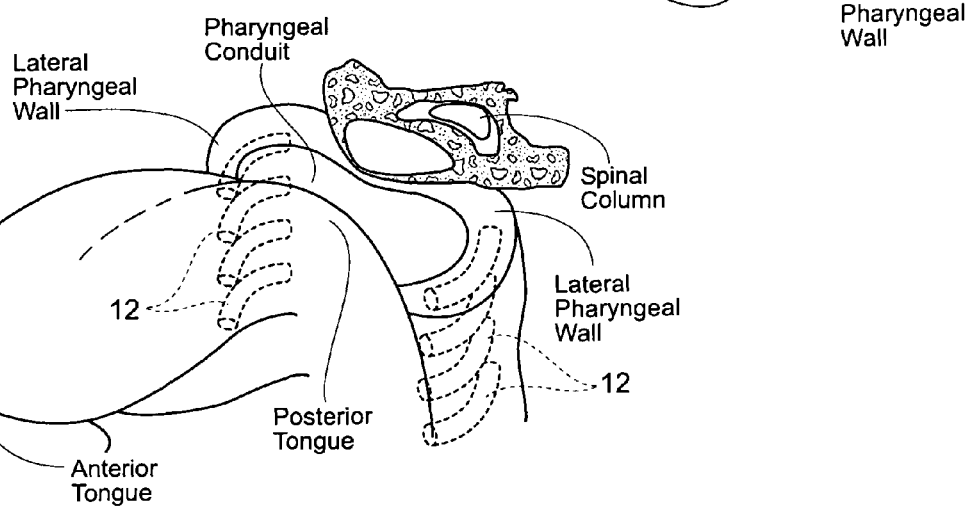
Fig. 17C

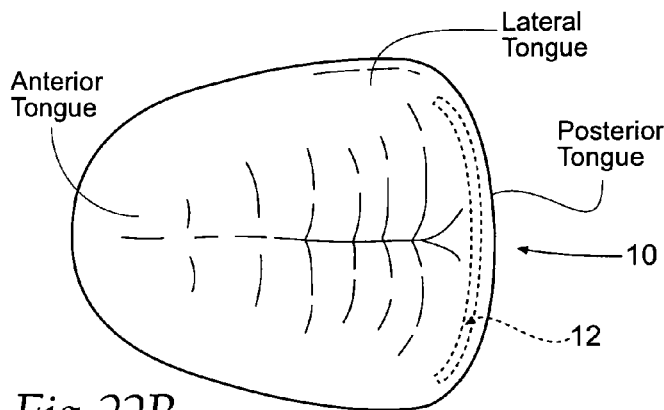
Fig. 22B
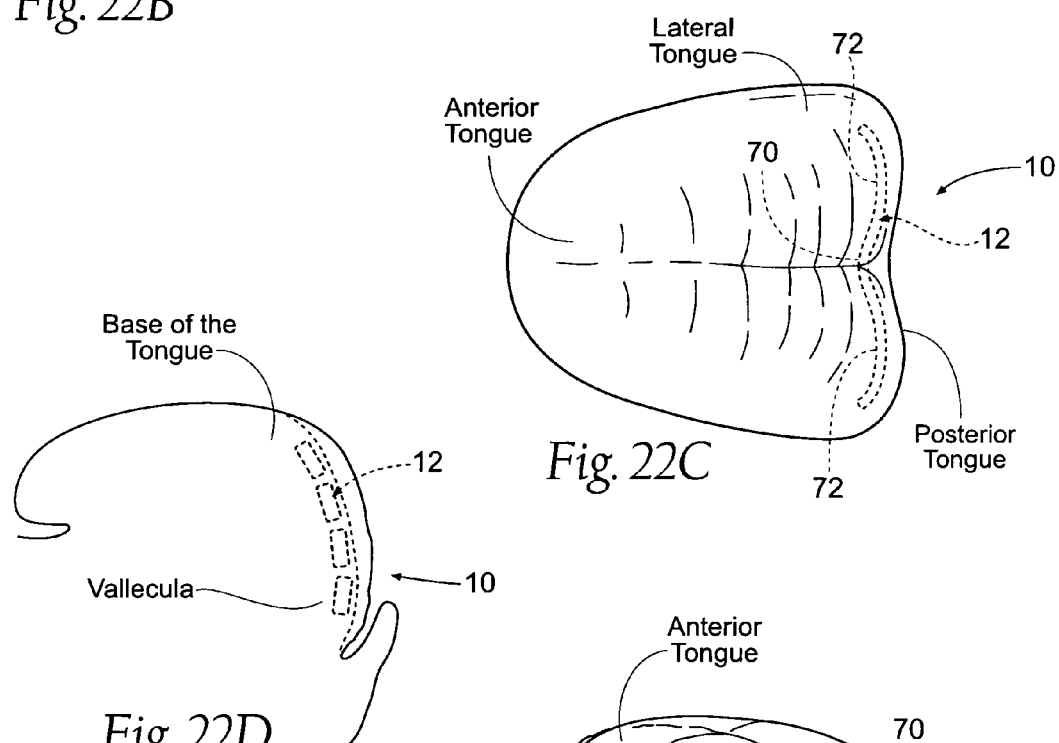
Fig. 22C
Fig. 22D
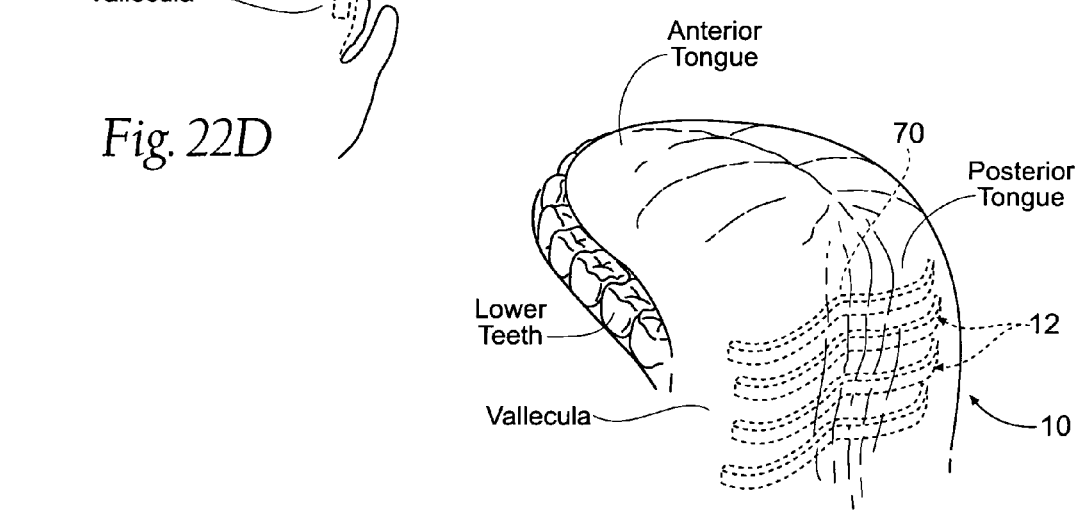
Fig. 22E

US 8,752,552 B2

DEVICES, SYSTEMS, AND METHODS TO FIXATE TISSUE WITHIN THE REGIONS OF BODY, SUCH AS THE PHARYNGEAL CONDUIT

RELATED APPLICATIONS

This application is a divisional of 5 application Ser. No. 10/718,254 filed 20 Nov. 2003, now U.S. Pat. No. 7,360,542, which is a continuation-in-part of U.S. patent application Ser. No. 10/656,861, now Pat. No. 7,188,627, filed Sep. 6, 2003 and entitled "Magnetic Force Devices, Systems, and Methods for Resisting Tissue Collapse within the 10 Pharyngeal Conduit" and a continuation-in-part of U.S. patent application Ser. No. 10/236,455, filed Sep. 6, 2002, now U.S. Pat. No. 7,216,648, and entitled "Systems and Methods for Moving and/or Restraining Tissue in the Upper Respiratory System". This application also claims the benefit of 15 U.S. Provisional Patent Application Ser. No. 60/441,639, filed Jan. 22, 2003, and entitled "Magnetic Splint Device and Method for the Treatment of Upper Airway Collapse in Obstructive Sleep Apnea, and the benefit of U.S. Provisional Patent Application 20 Ser. No. 60/456,164, filed Mar. 20, 2003 and entitled "Device and Method for Treatment of Sleep Related Breathing Disorders Including Snoring and Sleep Apnea," which are each incorporated herein by reference.

FIELD OF THE INVENTION

The invention is directed to devices, systems, and methods for the treatment of sleep disordered breathing including obstructive sleep apnea.

BACKGROUND OF THE INVENTION

I. The Characteristics of Sleep Apnea

First described in 1965, sleep apnea is a breathing disorder characterized by brief interruptions (10 seconds or more) of breathing during sleep. Sleep apnea is a common but serious, potentially life-threatening condition, affecting as many as 18 million Americans.

There are two types of sleep apnea: central and obstructive. Central sleep apnea, which is relatively rare, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. It is one of the several entities that make up the broader group of sleep disordered breathing (SDB). This group of disorders ranges from habitual snoring to OSA. Normally, the muscles of the upper part of the throat keep the airway open to permit air flow into the lungs. When the muscles of the upper airway relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" can be quite frequent. These breathing pauses are almost always accompanied by snoring between apnea episodes, although not everyone who snores has OSA.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all humans, the frequency of blockages will determine the seriousness of the disease and opportunity for health damage. When the incidence of blockage is frequent, corrective action should be taken.

II. Sleep and the Anatomy of the Upper Airway

As FIGS. 1A and 1B show, the upper airway consists of a conduit that begins at the nasal valve, situated in the tip of the nose, and extends to the larynx. Although all tissue along this conduit is dynamic and responsive to the respiratory cycle, only the pharyngeal conduit structures—the tissues in the region of the airway that starts behind the nasal cavity and ends in its connections to the supraglottic larynx—is totally collapsible. The pharyngeal structures and individual anatomic components within this region include the pharyngeal walls; the base of the tongue; the vallecula; the hyoid bone and its attachments; the soft palate with uvula, the palatine tonsils with associated pillar tissue; and the epiglottis.

The cross sectional area of the upper airway varies with the phases of the respiratory cycle. At the initiation of inspiration (Phase I), the airway begins to dilate and then to remain relatively constant through the remainder of inspiration (Phase II). At the onset of expiration (Phase III) the airway begins to enlarge, reaching maximum diameter and then diminishing in size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration. Schwab R J, Goldberg A N. *Upper Airway Assessment: Radiographic and other Imaging Techniques. Otolaryngol Clin North Am* 1998; 31:931-968.

Sleep is characterized by a reduction in upper airway dilator muscle activity. For the individual with obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx. Isono S. Remmers J, Tanaka A Sho Y, Sato J, Nishino T. *Anatomy of Pharynx in Patients with Obstructive Sleep Apnea and in Normal Subjects. J Appl Physiol* 1997: 82:1319-1326.

Although anatomic closure is often accentuated at specific sites, such as the velopharyngeal level [Isono, Ibid], studies of closing pressures [Isono, Ibid] supports dynamic fast MRI imaging that shows narrowing and collapse usually occurs along the entire length of the pharynx. Shellock F G, Schatz C J, Julien P, Silverman J M, Steinberg F, Foo T K F, Hopp M L, Westbrook P R. *Occlusion and Narrowing of the Pharyngeal Airway in Obstructive Sleep Apnea: Evaluation by Ultrafast Spoiled GRASS MR Imaging. Am J of Roentgenology* 1992: 158:1019-1024.

III. Prior Treatment Modalities

To date, the only modality that addresses collapse along the entire upper airway is mechanical positive pressure breathing devices, such as continuous positive airway pressure (CPAP) machines. All other modalities, such as various surgical procedures and oral appliances, by their nature, address specific sectors of the airway (such as palate, tongue base and hyoid-vallecula levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment in 6 months.

The need remains for simple, cost-effective devices, systems, and methods for reducing or preventing sleep disordered breathing events.

SUMMARY OF THE INVENTION

One aspect of the invention provides devices, systems and methods that employ static and/or kinetic force to fixate or brace tissue in targeted pharyngeal structures and individual anatomic components within the pharyngeal conduit, or within other anatomic structures. When used in the pharyngeal conduit, the devices, systems, and methods can serve to impede tissue collapse, when imminent, to maintain patency of the pharyngeal conduit. When used elsewhere, the devices, systems, and methods can serve different purposes, e.g., to assist in closing anatomic pathways.

In one embodiment, the devices, systems, and methods include at least one implanted structure. The implanted structure is sized and configured to remodel native tissue conditions within the targeted tissue region, by altering existing morphology and/or motility and/or shape of tissue that, if not altered, could lead to tissue collapse, particularly during the inspiration phase of the respiratory cycle. The implanted structure establishes tissue conditions that flexibly fixate or brace the tissue, to resist the collapse of tissue along the pharyngeal conduit when imminent, i.e., during sleep, but without significantly affecting the native tissue at times when tissue collapse is not imminent. The fixation or bracing function of the implanted structure can be accomplished by either static means, or kinetic means, or a combination thereof.

The targeted pharyngeal structures and individual anatomic components within this region can include, e.g., the pharyngeal walls; the base of the tongue; the vallecula; and the soft palate with uvula.

Another aspect of the invention provides devices, systems, and methods that brace or fixate tissue in targeted pharyngeal structures and/or individual anatomic components within the pharyngeal conduit by use of a pressure chamber, which is sized and configured to be located outside of the pharyngeal conduit and to hold a pressure that is less than atmospheric pressure. In one embodiment, the pressure chamber is sized and configured to hold a pressure that is less than a minimum pressure condition experienced in the pharyngeal conduit during a respiration cycle. The pressure chamber can be sized and configured, e.g., to be worn about a neck.

The devices, systems, and methods can be used to treat airway collapse and increased airway resistance associated with the entire spectrum of obstructive sleep-disordered breathing. The devices, systems, and methods can also be used to lend upper airway support in neurological associated dystonic disorders.

Other features and advantages of the invention shall be apparent based upon the accompanying description, drawings, and claims.

DESCRIPTION OF THE DRAWINGS

FIG. 1B is a superior view taken generally along line 1B-1B in FIG. 1.

FIGS. 8A to 8D show an implanted kinetic force structure of a type shown in FIG. 2A that is shaped due to magnetic forces, FIGS. 8C and 8D showing the structure implanted in the pharyngeal wall for purposes of illustration, and FIG. 8D showing the structure juxtaposed with another magnetic structure implanted in the base of the tongue.

FIG. 15 show an implanted static and/or kinetic force structure of a type shown in FIG. 2A that carries a tissue in-growth surface.

FIGS. 16A and 16B and FIGS. 17A to 17C show static and/or kinetic force structures of a type shown in FIG. 2A implanted in horizontal arrays in targeted pharyngeal structures and individual anatomic components within the pharyngeal conduit.

FIGS. 22A to 22E shows an illustrative embodiment of a system of the type shown in FIG. 2A that includes static and/or kinetic force structures implanted in the tongue and adjacent anatomic structures.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Systems to Fixate or Brace Tissue

A. Implanted Force Systems

Figure 2A:
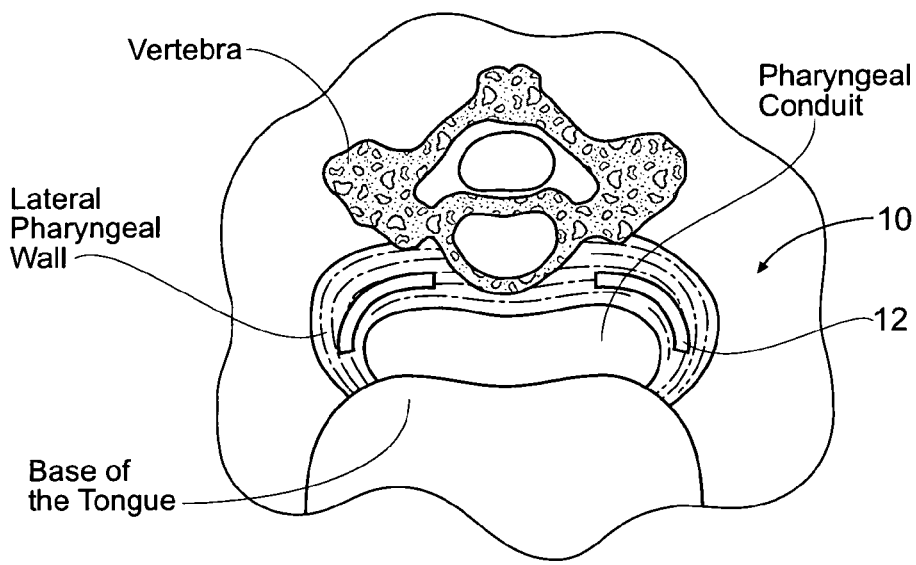
FIG. 2A shows in a diagrammatic way a force system that uses implanted structures to fixate or brace tissue in targeted pharyngeal structures and individual anatomic components within the pharyngeal conduit.

FIG. 2A shows in a diagrammatic way a force system 10 that, in use, fixates or braces tissue in targeted pharyngeal structures and individual anatomic components within the pharyngeal conduit using one or more implanted structures 12. The force system 10 thereby impedes tissue collapse, when imminent, to maintain patency of the conduit. The system 10 can be used to treat airway collapse and increased airway resistance associated with the entire spectrum of obstructive sleep-disordered breathing. The system 10 can also be used to lend upper airway support in neurological associated dystonic disorders.

In one basic form, the force system 10 comprises at least one fixation or bracing structure 12 (shown in FIG. 2A), which is sized and configured to be implanted in a targeted tissue region within the pharyngeal conduit. The size and configuration of the implanted structure 12 are selected to remodel native tissue conditions within the targeted tissue region, by altering existing morphology and/or motility and/or shape of tissue that, if not altered, could lead to tissue collapse, particularly during the respiratory cycle. The implanted structure 12 establishes tissue conditions that fixate or brace the tissue, to resist collapse along the pharyngeal conduit when imminent, i.e., during sleep, but without significantly stiffening the native tissue at times when tissue collapse is not imminent.

Figure 1A:
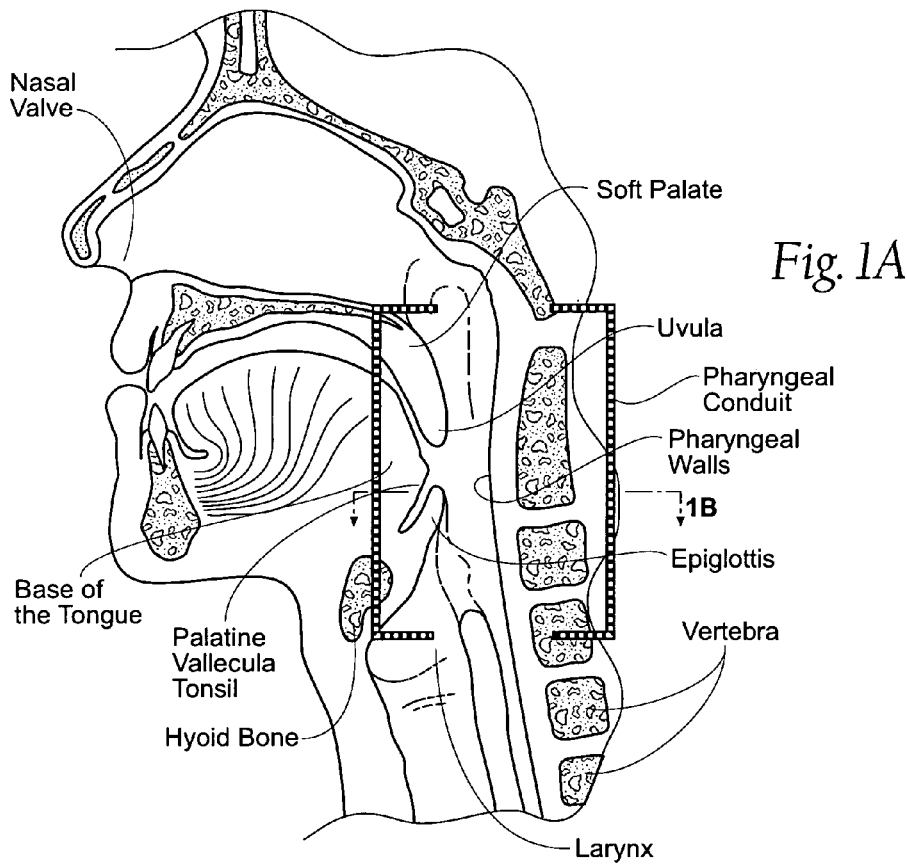
FIGS. 1A and 1B are anatomic views of the upper airway in a human, showing certain pharyngeal structures and individual anatomic components within the pharyngeal conduit, FIG. 1A comprising a lateral view
Figure 1B:
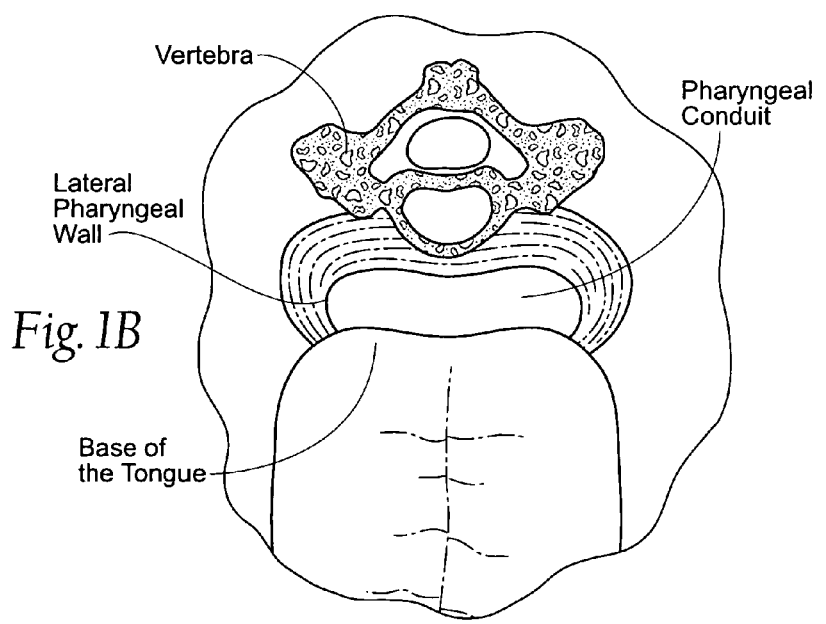

The targeted pharyngeal structures and individual anatomic components within this region can include the pharyngeal walls; the base of the tongue; the vallecula; the soft palate with uvula; the palatine tonsils with associated pillar tissue; and the epiglottis. These anatomic regions are shown in FIGS. 1A and 1B. Representative examples of embodiments of magnetic force systems 10 in certain targeted pharyngeal structures and individual anatomic components within the pharyngeal conduit will be described in greater detail later.

The fixation or bracing function of the implanted structure 12 can be accomplished by static means. The static means conditions the tissue by virtue of inherent material properties and shape of the structure 12. For example, a given static implanted structure 12 can take the form of a fluid or slurry that is injected into tissue to form a gel or a solid matrix having a shape and/or material properties that apply the static fixation or bracing force to adjacent tissue. A static implanted structure 12 can also take the form of a pre-shaped metal and/or polymer and fabric and/or textile and/or ceramic structure having inherent material properties and shape that, once implanted, conditions the tissue. In either situation, the static conditioning remodels the morphology and/or motility and/or shape of adjacent tissue. Representative embodiments of force systems 10 comprising implanted static structures 12 will be described in greater detail later.

The fixation or bracing function of the implanted structure 12 can also be accomplished by kinetic means. The kinetic means exerts dynamic forces that react to kinetic forces within tissue. The reactive dynamic forces can be generated, e.g., by magnetic field forces and/or spring-like mechanical properties and/or elastic mechanical properties. The reactive dynamic forces not only impart a desired shape to the implant, but also imparting a dynamic resistance to or bias against a change in the shape. In this arrangement, for example, the implanted kinetic structure 12 can comprise a metal and/or plastic and/or fabric and/or textile and/or ceramic material that possesses a desired spring constant or elastic loading to continuously exert a dynamic reactive force, e.g., like a mechanical spring. Implanted kinetic structures 12 can also be made from a metal and/or plastic and/or fabric and/or ceramic material, which selectively assumes a shaped, elastically loaded condition in response to an activating force, for example, magnetism or temperature conditions or electrical energy or electromagnetic force. The reactive dynamic forces exerted impart a desired new morphology and/or motility and/or shape to adjacent tissue, and also resist a change in these conditions. Representative embodiments of force systems 10 comprising kinetic implanted structures 12 will be described in greater detail later.

The fixation or bracing function of the implanted structure 12 imparts improved comfort, tolerance, and bio-acceptance to the implanted structure for the patient. The fixation or bracing function is achieved without indiscriminate dampening (i.e., stiffening) the spring constant of native tissue in the pharyngeal conduit (which is not desirable). The fixation or bracing function is achieved due to the controlled application of static and/or kinetic forces that push or pull on tissue, without themselves imparting stiffness to the tissue in the pharyngeal conduit. The size and configuration of the implanted structures are selected with the ease and bio-comfort of implantation in mind, while at the same time providing sufficient static and/or kinetic forces to resist tissue collapse when collapse is imminent, taking into account the anatomy of the region of implantation and orientation of other components of the system 10. The implanted structures 12 thereby provide conformability, tolerance, and comfort for the patient, without significantly dampening the spring constant of native tissue.

Prior to implanting a given structure 12, tissue in the targeted tissue region may be dilated, e.g., by use of a trocar or expandable structure, e.g., a balloon or inflatable structure, to open a tissue space to receive the structure. During dilation, the tissue space may be deliberately sized and shaped, so that the resulting implanted structure best conforms to the size, shape, and physical characteristics to bring about the desired physiologic response.

B. Pressure Chamber Systems

Figure 2B:
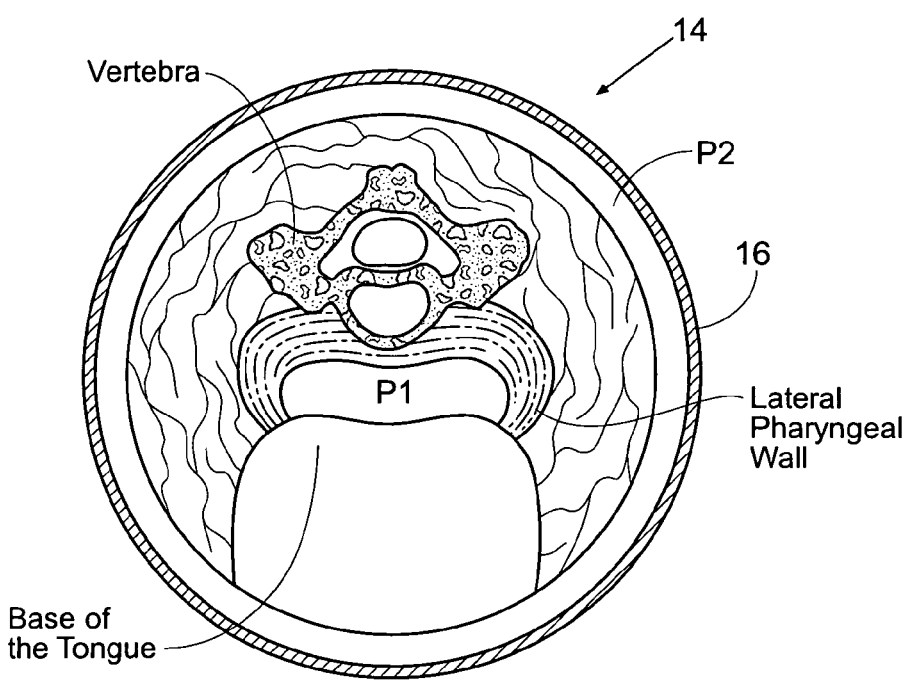
FIG. 2B shows in a diagrammatic way a system that uses pressure to fixate or brace tissue along the pharyngeal conduit.

FIG. 2B shows in a diagrammatic way a pressure chamber system 14 that, in use, fixates or braces tissue in targeted pharyngeal structures and individual anatomic components within the pharyngeal conduit by altering the differential between internal pressure existing within the pharyngeal conduit (P1 in FIG. 2B) and external pressure existing outside the pharyngeal conduit (P2 in FIG. 2B). More particularly, the pressure chamber system 14 lowers, in a localized region surrounding all or a portion of the pharyngeal conduit, the external pressure to a pressure condition (P2) that is less than atmospheric pressure and desirably less than the minimum expected pharyngeal pressure (P1), which typically occurs during the inhalation phase of the respiratory cycle. The pressure chamber system 14 desirably creates in this localized region a pressure differential that impedes tissue collapse to maintain patency of the conduit. The purpose of the pressure chamber system 14 is to desirably nullify the vector sum of the extralumenal forces on the conduit, to make it de-compressive. These forces are created by atmospheric pressure, gravity, contractive forces caused by upper airway muscle activity, and inward forces caused by subatmospheric luminal pressure generated during inhalation.

Like the force system 10, the pressure chamber system 14 can be used to treat airway collapse and increased airway resistance associated with the entire spectrum of obstructive sleep-disordered breathing. The pressure chamber system 14 can also be used to lend upper airway support in neurological associated dystonic disorders.

In one basic form, the pressure chamber system 14 comprises at least one external pressure chamber 16 (shown in FIG. 2B), which is sized and configured to be worn by an individual, when desired, about a targeted tissue region or regions within the pharyngeal conduit. The targeted pharyngeal structures and individual anatomic components within this region can include the pharyngeal walls; the base of the tongue; the vallecula; the soft palate with uvula; the palatine tonsils with associated pillar tissue; and the epiglottis.

The pressure chamber 16 establishes a localized pressure condition (P2) about the targeted tissue region that is less than atmospheric pressure and desirably less than the minimum-expected pressure condition present in the pharyngeal conduit (P1). Exposed to a localized pressure differential that is more negative than ambient conditions, tissue along the pharyngeal conduit resists collapse when collapse is imminent, i.e., upon inhalation during sleep. The pressure chamber 16 can be removed during waking hours.

Illustrative embodiments of implanted force systems 10 and external pressure chamber systems 14 will now be described.

II. Illustrative Implanted Static Structures Useable with the Force System

A. Injected Fluids and/or Slurries

Figure 3A:
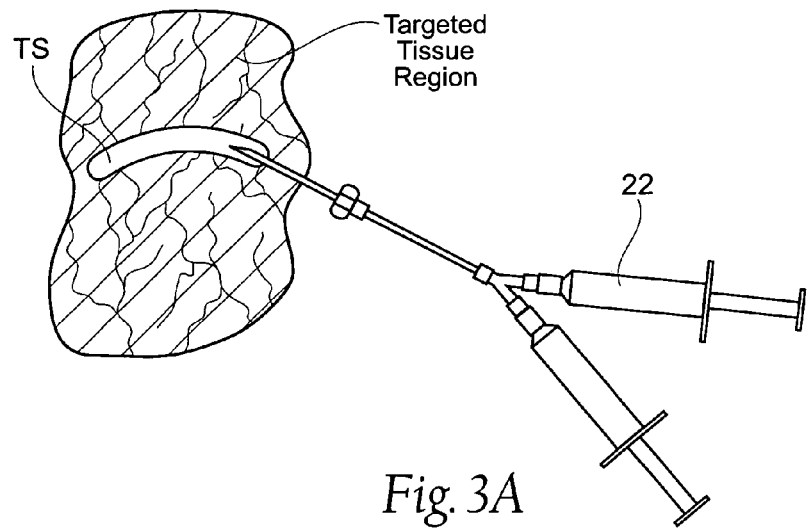
FIGS. 3A to 3C show an implanted static force structure of a type shown in FIG. 2A that includes a material injected into a targeted tissue region.
Figure 3B:
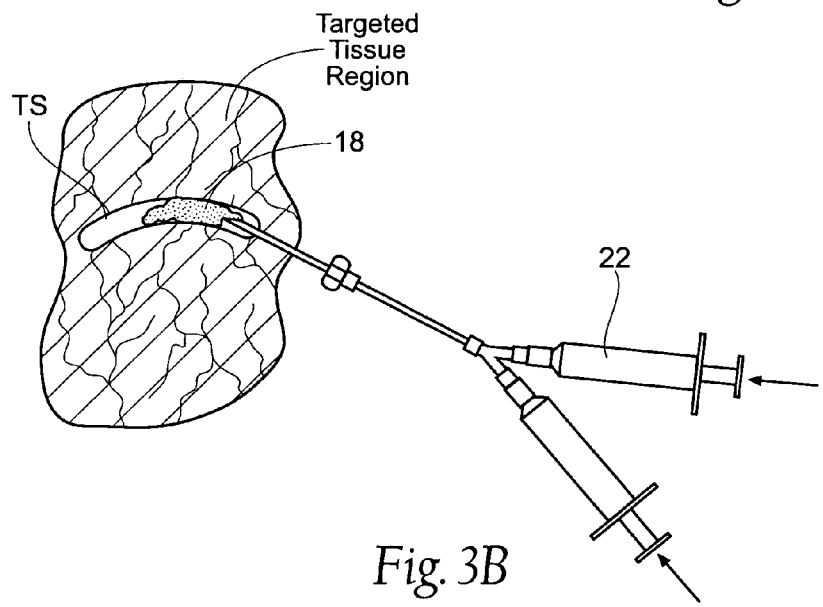
Figure 3C:
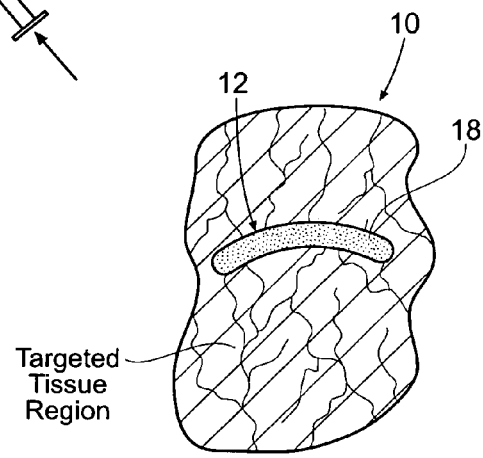

As FIGS. 3A to 3C show, an implanted static structure 12 can include an injected material 18 comprising one or more biocompatible liquid components, or one or more solid biocompatible components carried in one or more liquid biocompatible components. The material 18 can be injected as a liquid or slurry into a targeted tissue region, e.g., by a syringe 22 or the like (as FIG. 3B shows), which can comprise, e.g., the tongue, the vallecula, a pharyngeal wall, or the soft palate/uvula. In one arrangement, upon mixing, the components cross-link, polymerize, or otherwise chemically react to create an in situ biocompatible, non-liquid, static mechanical implant structure 12 (as FIG. 3C shows). Implanted static structures 12 formed in situ from injected materials 18 are well suited for implantation in targeted pharyngeal structures and other anatomic components within the pharyngeal conduit.

Prior to injection of the material, tissue in the targeted tissue region may be dilated (see FIG. 3A), e.g., by use of a trocar or expandable structure, to open a tissue space TS to receive the in situ-setting fluid or slurry material 18. During dilation, the tissue space TS may be deliberately sized and shaped, so that the resulting implant material 18 injected into it will possess the size, shape, and physical characteristics to bring about the desired physiologic response.

The biocompatible liquid component may comprise, e.g., an Elastin™ media. Alternatively, the liquid component may comprise an oil or low viscosity liquid that is biocompatible to impart the desired new morphology and/or motility and/or shape to surrounding tissue. The solid component may be a polyvinyl acetate (PVA) or foam that is appropriately sealed to provide biocompatibility. Other materials such as silicone rubber, elastomeric polymers and polytetrafluoroethylene (Teflon® Material, from DuPont) may also be selected. Alternatively, a powder, small beads, or shavings of solid material can be mixed with a slurry or liquid.

As FIG. 3C shows, the injected liquid or slurry may be formulated to set in situ, to form an implanted static implant 12, possessing the shape, position and mechanical properties to impart the desired new morphology and/or motility and/or shape to surrounding tissue.

Figure 4A:
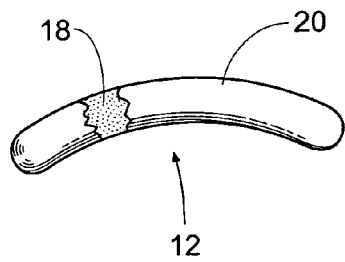
FIGS. 4A to 4D show an implanted static force structure of a type shown in FIG. 2A that includes a material injected into an expandable container implanted in a targeted tissue region.
Figure 4B:
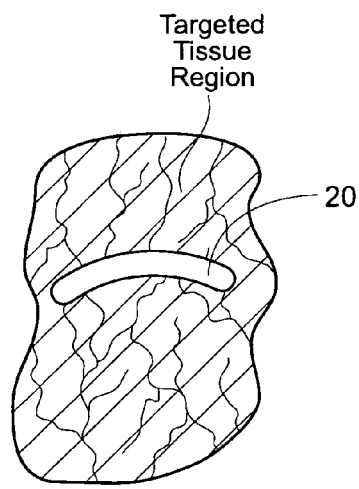

Alternatively (see FIGS. 4A to 4D), the fluid or slurry material 18 may be injected into an expandable container 20 (FIG. 4A) that is itself implanted in a targeted tissue region (FIG. 4B). As FIG. 4A shows, the container is desirably pre-shaped, to assume the desired inflated shape, position, and mechanical properties.

Figure 4C:
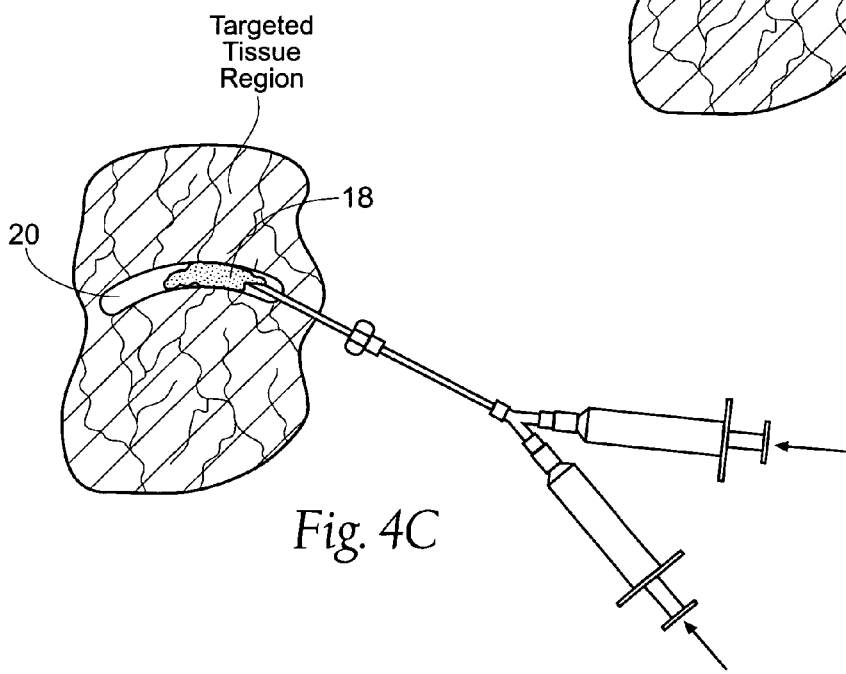
Figure 4D:
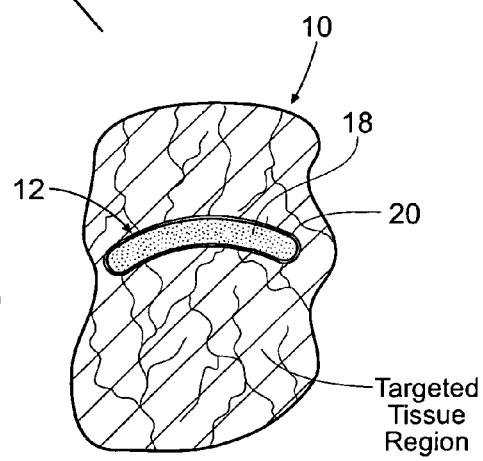

Once suitably implanted, the container 20 is inflated by infusion of the fluid or slurry material 18, which is dispensed, e.g., from a syringe 22 or the like (see FIG. 4C). In one arrangement, the injected liquid or slurry material 18 may be formulated to set in situ within the container 20 (see FIG. 4D), the container and its contents serve as an implanted static implant 12, possessing the shape, position and mechanical properties to impart the desired new morphology and/or motility and/or shape to surrounding tissue, or to otherwise achieve the desired physiologic response. It should be appreciated that, when an implanted container 20 is used to house the injected material 18, saline or a fluid or slurry that does not set or cure in situ may be used to form an implanted kinetic structure 12. Furthermore, the fluid or slurry material 18 may be formulated to be injected as a gel that need not set or cure to perform its intended function.

The container 20 may comprise a bioresorbable material, such as polyglycolic acid, a polymer used for resorbable sutures and other devices within the body. In this arrangement, once the container 20 is resorbed, only the in situ-setting fluid of slurry material 18 will remain to serve as the implanted kinetic structure 12.

B. Shaped Static Structures

Figure 5A:
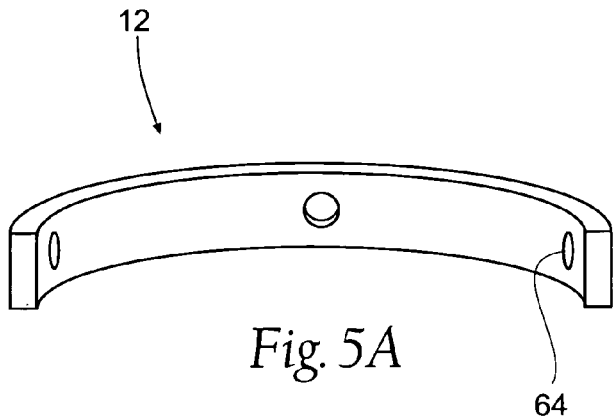
FIGS. 5A and 5B show an implanted static force structure of a type shown in FIG. 2A that is formed from a pre-shaped material, FIG. 5B showing the structure implanted in the vallecula for purposes of illustration.

As FIG. 5A shows, an implanted static structure 12 can be formed—e.g., by bending, shaping, joining, machining, molding, braiding, assembly, or extrusion—from a biocompatible metallic and/or polymer and/or fabric and/or textile and/or ceramic material, or a metallic and/or polymer and/or fabric and/or textile and/or ceramic material that is suitably coated, impregnated, or otherwise treated with a material to impart biocompatibility, or a combination of such materials. For example, pre-shaped, static structures 12 can be formed from acetal resins (Delrin® material, Celcon® material), Teflon® material, and/or silicone rubber compounds.

Figure 5B:
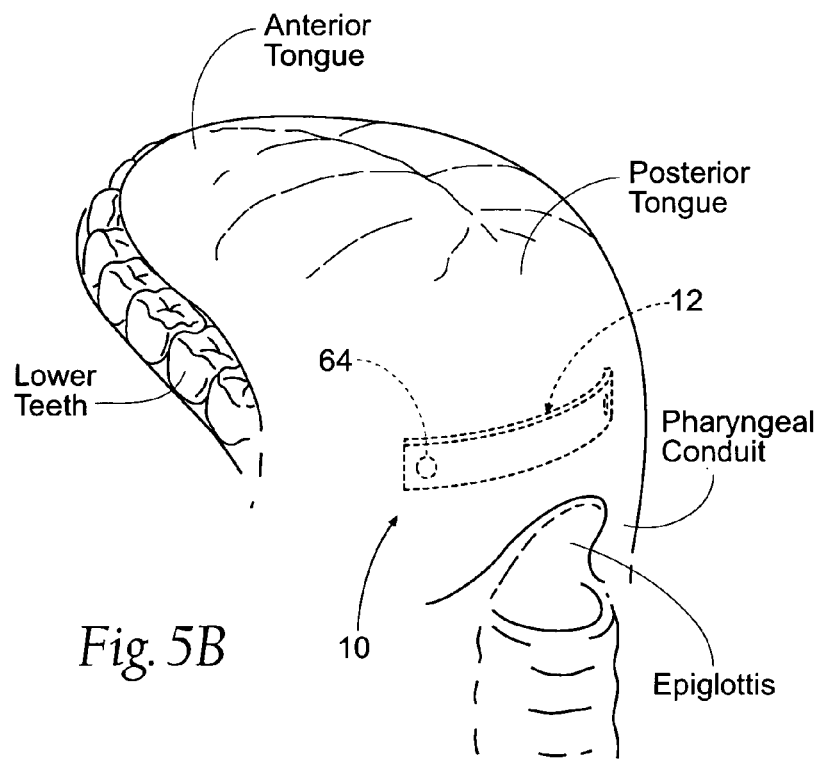

Implanted static structures 12 formed from pre-shaped metallic and/or polymeric and/or fabric and/or textile and/or ceramic materials are well suited for implantation in the tongue, the vallecula, or soft palate, as well as other targeted pharyngeal structures and other anatomic components within the pharyngeal conduit. FIG. 5B shows the pre-shaped static structure 12 implanted, for the purpose of illustration in the vallecula. Once suitably implanted in a targeted tissue region, the static implant 12 possesses the shape, position and mechanical properties to impart the desired new morphology and/or motility and/or shape to surrounding tissue, or to otherwise achieve the desired physiologic response.

C. Bending Structures

Figure 6A:
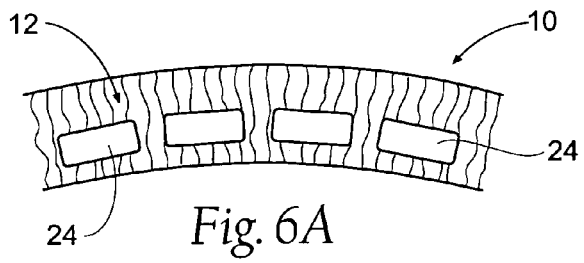
FIGS. 6A to 6F show various embodiments of an implanted static force structure of a type shown in FIG. 2A that is formed from an array of individual, spaced apart implants that move together as a result of tissue compression to resist tissue collapse along the pharyngeal conduit.

As FIG. 6A shows, an implanted static structure 12 can be formed by an array of individual implants 24 sized and configured to be spaced-apart along an arc. The radius of the arc and the spacing between the individual implants 24 along the arc are predetermined, so that individual implants 24 will move successively closer together as the tissue develops the morphology and/or motility and/or shape conducive to collapse. The radius of the arc and spacing distance are preselected so that, before tissue collapse occurs (see FIG. 6B), spacing between the individual implants 24 will diminish, compressing tissue between them. The spacing between individual implants 24 may disappear, as the implants 24 come into contact with or abutment against each other. When tissue compression occurs, the array of implants 24 possesses a composite shape, position and mechanical properties to impart a desired new morphology and/or motility and/or shape to surrounding tissue, to resist tissue collapse. Still, when collapse of the tissue is not imminent (see FIG. 6A), the implants 24 occupy a spaced-apart, non-contiguous relationship, which does not compress tissue or significantly affect the morphology and/or motility and/or shape to surrounding tissue.

Figure 6B:
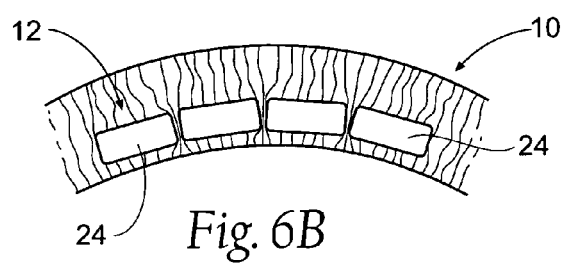
Figure 6C:
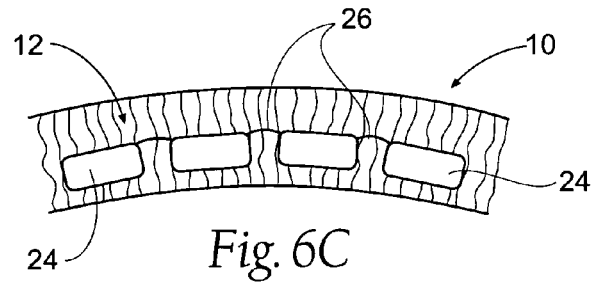
Figure 6D:
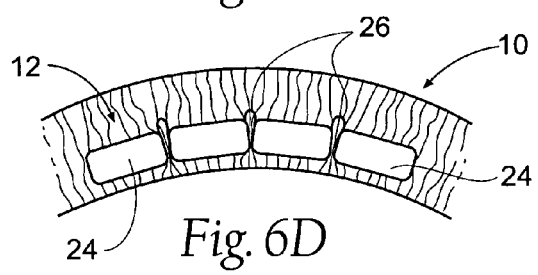

As FIGS. 6C and 6D show, individual, spaced-apart implants 24 within the array may be linked together, e.g., by plastic and/or metal and/or fabric and/or textile and/or ceramic material 26, to help keep the implants 24 in a desired spatial relationship. The mechanical properties of the linking material 26 also affects the mechanical properties of the array prior to tissue compression.

Figure 6E:
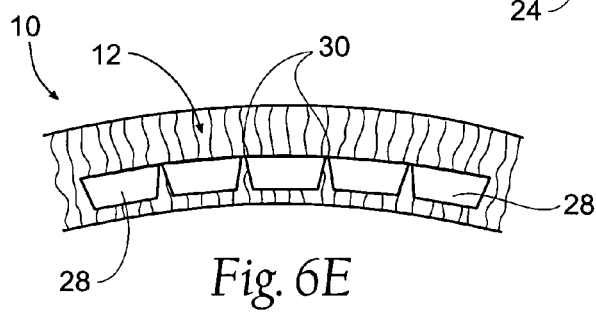
Figure 6F:
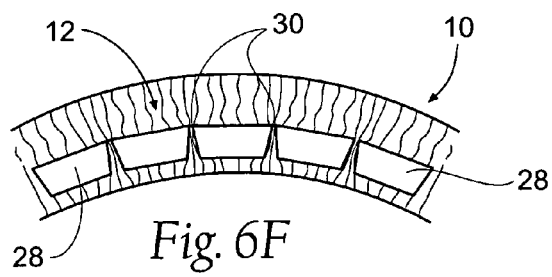

As FIGS. 6E and 6F show, the implant 12 can comprise a body 28 having one or more preformed hinge points 30. When collapse of the tissue is not imminent (see FIG. 6E), the hinge points 30 are open, and the body 28 does not significantly affect the morphology and/or motility and/or shape to surrounding tissue. However (see FIG. 6F), the hinge points 30 close as the tissue develops the morphology and/or motility and/or shape conducive to collapse. With the hinge points 30 closed, the body 28 possesses the shape, position and mechanical properties to impart a desired new morphology and/or motility and/or shape to surrounding tissue, to resist tissue collapse.

When the hinge points 30 are closed, the mechanical properties of the material of the body 28 determine the magnitude of the resistance to tissue collapse. The material of the hinged body 28 (which can comprise plastic and/or metal and/or fabric and/or textile and/or ceramic) can be stiff or flexible, or elastic or in-elastic, or combinations thereof. If elastic, the hinged body 28 can function, when the hinge points 30 are closed, as a kinetic implant structure 12, as will be described below. The hinge points 30 can also be varied in terms of closure angle and spacing, to provide along the length of the hinged body 28, regions of differing resistance to closure. The hinged body 28 can also be made of materials having different mechanical properties, to provide along the length of the hinged body regions of differing flexibility and/or elasticity.

III. Illustrative Implanted Kinetic Structures Useable with the Force System

A. Continuously Kinetic

1. Shaped Springs

Figure 7A:
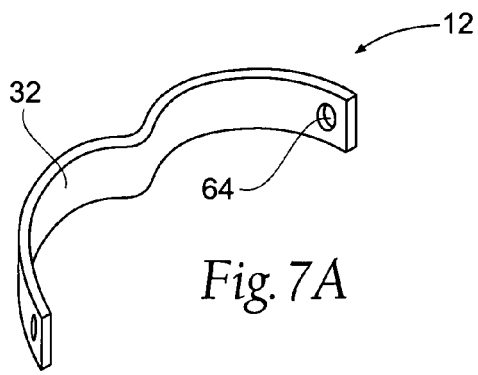
FIGS. 7A and 7B show an implanted kinetic force structure of a type shown in FIG. 2A that is formed from a spring-loaded material, FIG. 5B showing the structure implanted in the pharyngeal wall for purposes of illustration.

As FIG. 7A shows, an implanted kinetic structure 12 can exert a dynamic reactive force by virtue of elasticity or spring bias. The elasticity or spring bias places the kinetic structure under normal compression, which imparts a desired shape to the structure and also provides an elastic resistance to a change in that shape.

Spring-biased kinetic structures 12 formed from pre-shaped metallic and/or polymeric and/or fabric and/or textile and/or ceramic materials are well suited for implantation in the tongue, the vallecula, soft palate, a pharyngeal wall, as well as other targeted pharyngeal structures and other anatomic components within the pharyngeal conduit. FIG. 6B shows an illustrative spring-biased kinetic structure implanted, for purposes of illustration, in a pharyngeal wall.

Figure 7B:
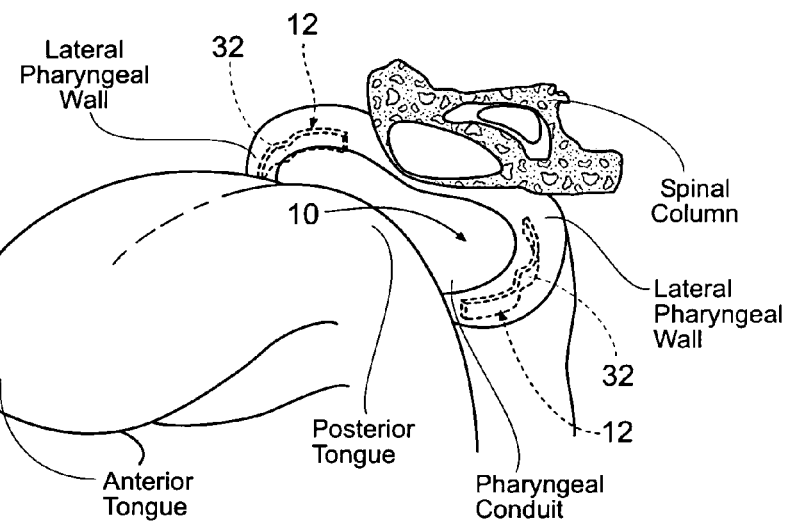

The structure 12 is formed, e.g., from a shaped elastic or super-elastic plastic or metal or alloy material 32. The structure 12 includes a preformed biased toward a desired shape, which, in the illustrated embodiment is shown to be a curved configuration conducive to bracing the tissue in the pharyngeal wall against collapse into the airway. Movement of the tissue into the airway is kinetically resisted by the spring-biased elasticity of the structure 12. The structure 12 is shown in FIGS. 7A and 7B to be a flat strip. However, the structure can be wire-formed, or tubular, or possess virtually any other cross sectional configuration.

Figure 7C:
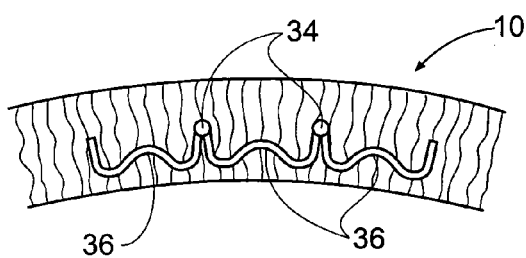
FIGS. 7C and 7D show an implanted kinetic force structure of a type shown in FIG. 2A that is formed from an array of individual, spring-loaded structures that are hinged together to resist tissue collapse along the pharyngeal conduit.
Figure 7D:
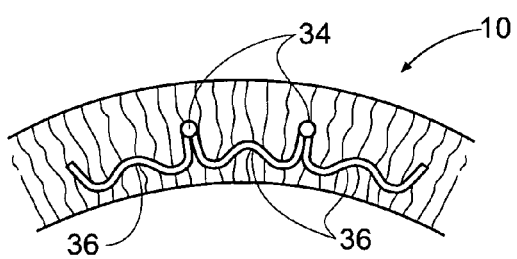

As FIGS. 7C and 7D show, individual spring-like structures 36 exerting dynamic reactive force by virtue of elasticity or spring bias can be joined by hinge points 34. When collapse of the tissue is not imminent (see FIG. 7C), the hinge points 34 are open, and the hinged bodies 36 do not significantly affect the morphology and/or motility and/or shape to surrounding tissue. However (see FIG. 7D), the hinge points 34 close as the tissue develops the morphology and/or motility and/or shape conducive to collapse. With the hinge points 34 closed, and the bodies 35 collectively assume a spring-loaded condition to impart a desired new morphology and/or motility and/or shape to surrounding tissue, to resist tissue collapse. When the hinge points 34 are closed, the collective elastic or spring-biased mechanical properties of the individual spring-loaded bodies 36 kinetically resist tissue collapse. As previously discussed with respect to the hinged body 28 shown in FIGS. 6E and 6F, the hinge points 34 can be varied in terms of closure angle and spacing, to provide along the length of the hinged body 36, regions of differing resistance to closure. The individual spring-like structures 36 linked by the hinges 34 can also be made of materials having different elastic or spring-biased properties, to provide along the length of the hinged body regions of differing kinetic resistance to tissue collapse.

2. Shaped Magnetic Arrays

An implanted kinetic structure 12 can also exert a dynamic force by virtue of magnetic forces. The magnetic forces impart a desired shape to the implant 12, while also providing a magnetic field resistance to or bias against shape change. FIGS. 8A(1), (2), and (3) and 8B show an illustrative magnetically shaped array of permanent magnets 38 mounted on a flexible, inelastic carrier 40. The carrier 40 may carry one or more rows of magnets 38.

The permanent magnets 38 on the carrier 40 are characterized as showing resistance to external demagnetizing forces once being magnetized. Examples of known permanent magnet materials include alloys of Neodymium-Iron-Boron (Nd-FeB), alloys of Aluminum-Nickel-Cobalt (AlNiCo), and Samarium Cobalt (SmCo). These materials are typically coated with Nickel. An electromagnet (current flowing through a coil of wire) can be substituted for a permanent magnet.

The permanent magnets 38 on the carrier 40 each generate an external magnetic field. As FIG. 8A(1) shows in diagrammatically, the permanent magnets 38 are arranged on the carrier 40 with like magnetic poles facing each other (North-North or South-South). According to physical laws, poles of like polarity repel each other with a magnetic force. The force of magnetic repulsion depends on the strength of the magnets and the distance between the poles. The permanent magnets 38 on the carrier 40 can also be arranged with the same poles facing the carrier 40, as shown in FIGS. 8A(2) and 8A(3). According to magnetic force calculations and finite element analysis, permanent magnets 38 like that shown in FIG. 8A(1), (2), or (3)—having the same poles facing the same direction—will repel each other if they are arranged in close proximity.

As FIG. 8B shows, the magnetic repulsion between neighboring magnets 38 bends the flexible carrier 40. Furthermore, the repelling force between neighboring magnets 38 gets stronger as distance between the poles decreases, and it is this continuous, dynamic force that resists straightening of the carrier 40 out of its magnetically set shape. This dynamic, magnetically induced resistance to shape change, in turn, exerts a dynamic force on neighboring tissue, to impart a desired new morphology and/or motility and/or shape to the tissue, together with a corresponding resistance to change in this condition, to achieve the desired physiologic response.

The carrier 40 is desirably made from a material that imparts biocompatibility, durability, and flexibility to the magnetic array. The carrier 40 may be made, e.g., of a flexible or semi-rigid material such as polycarbonate, silicone rubber, polyurethane, etc, or a flexible or semi-rigid plastic and/or metal and/or fabric and/or textile and/or ceramic material. The material of the carrier 40 can enclose the magnets 38, or the magnets 38 can be carried on the surface of the carrier 40. The spacing between the magnets 38 on or within the carrier 40 provides the requisite flexibility desired. The individual magnets 38 can have various geometries—rectangular, cylindrical, spherical, oval, etc.—as long as the desired physiologic response is achieved.

Flexible magnetically shaped structures 12 are well suited for implantation in targeted pharyngeal structures and other anatomic components within the pharyngeal conduit, e.g., the tongue, vallecula, soft palate/uvula, and a pharyngeal wall. FIG. 8C shows magnetically shaped structures 12 implanted, for the purpose of illustration, in pharyngeal walls. A magnetically shaped structure 12 can implanted alone, e.g., in a pharyngeal wall, or in conjunction with other magnetically shaped structures, as FIG. 8C shows.

As FIG. 8D shows, one or more magnetically shaped structures 12 in the pharyngeal wall can be juxtaposed to one or more permanent magnet structures 42 implanted in the posterior of the tongue. The magnets in the structures 12 and the magnet structures 42 in the tongue possess the same magnetic orientation. The repelling force between the opposing tongue magnet(s) and pharyngeal wall structures shape the pharyngeal wall structures in the manner described above. This juxtaposition of magnets resists collapse of the airway as the tissue relaxes and comes into proximity, particularly during Phase IV of the respiratory cycle. Other arrangements are possible, as will be described in greater detail later.

B. Selectively Kinetic

1. Shape Memory Structures

Figure 9A:
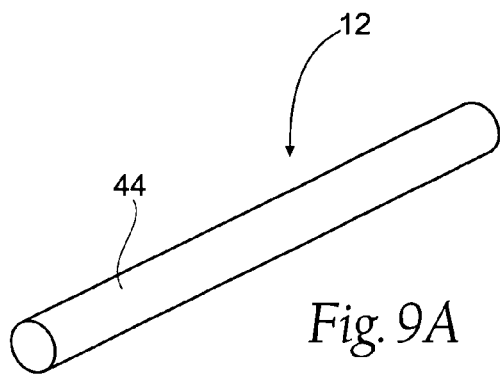
FIGS. 9A and 9B show an implanted kinetic force structure of a type shown in FIG. 2A that includes a shape-memory material that assumes a predetermined shape in response to an applied activation energy, FIG. 9A showing the structure before shape activation, and FIG. 9B showing the structure after shape activation.

An implanted kinetic structure 12 (see FIG. 9A) can exert a dynamic force by virtue of a selectively activated shape memory. In this arrangement, the implanted kinetic structure 12 is made from a class of materials 44 that have the ability to return to remembered shapes when activated by an external stimulus (see FIG. 9B). The structures 12 can be made from, e.g., shape memory alloys, shape memory polymers, or ferromagnetic shape memory alloys. Illustrative embodiments follow.

a. Shape Memory Materials

Figure 9B:
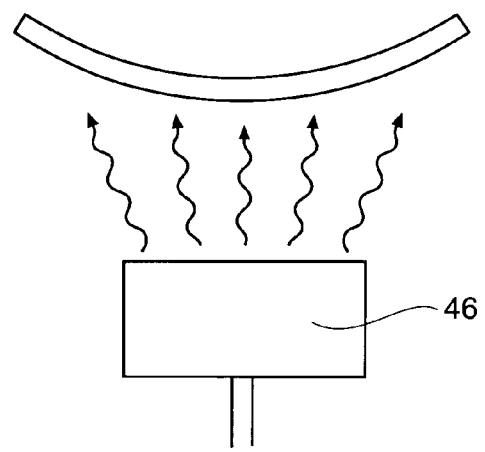

An implanted kinetic structure 12 can comprise a shape memory metal material 44 that assumes a predetermined, remembered shape in response to an applied activation energy 46 (see FIG. 9B). The activation energy 46 can comprise, e.g., electrical energy, mechanical energy, thermal energy, electromagnetic energy, acoustic energy, or light energy.

The shape memory material 44 can comprise an alloy, e.g., Nitinol® alloy (an alloy consisting of nickel and titanium), and copper based alloys, most commonly Cu—Zn—Al and Cu—Al—Ni. The shape memory material 44 can also comprise a shape memory polymer.

Figure 10A:
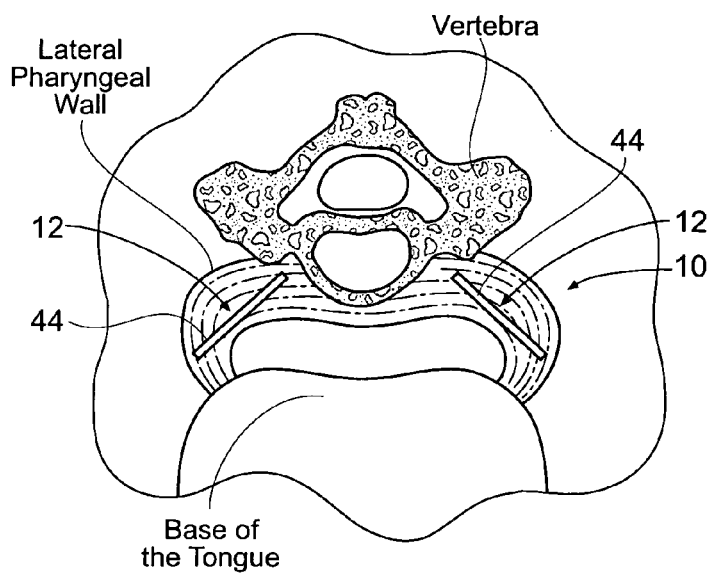
FIGS. 10A to 10D show an implanted kinetic structure of the type shown in FIGS. 9A and 9B implanted, for the purpose of illustration in a pharyngeal wall, FIG. 10C showing the structure being shape activated by use of an external collar, and FIG. 10D showing the structure being shape activated by use of a wand inserted in the oral cavity.
Figure 10B:
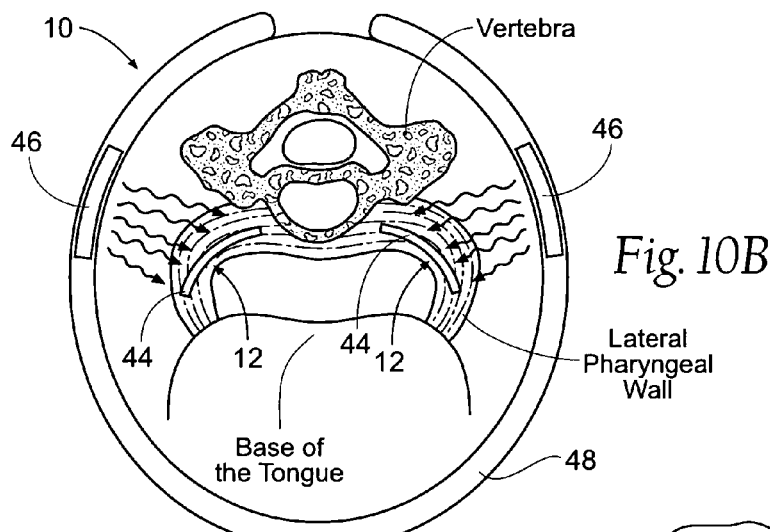

FIG. 10A shows an implanted kinetic structure 12 made, e.g., of a Nitinol® shape memory alloy. Shape memory kinetic structures 12 are well suited for implantation in the tongue, the vallecula, or the soft palate, as well as other targeted pharyngeal structures and other anatomic components within the pharyngeal conduit. In FIG. 10A, the structure 12 is implanted, for the purposes of illustration, in the pharyngeal wall. As shown in FIG. 10A, the structure 12 possesses relatively compliant mechanical properties at certain temperature conditions, which is sometimes called the soft martensitic phase. In response to increased temperature conditions, the structure 12 assumes less compliant mechanical properties (see FIG. 10B), accompanied by accelerated shape change. This is sometimes called the hard austenitic phase. In this phase (as shown in FIG. 10B), the structure 12 provides a dynamic resistance to shape change. In the illustrated embodiment, the change in temperature conditions is brought about by an external activation energy source 46 that is used when activation is desired. The activation energy source 46 can be worn by the individual (see FIGS. 10B and 10C), e.g., carried by a collar 48 secured about the neck of the individual. The activation source 46 (see FIG. 10D) can also be carried on a wand 50 that is placed in the oral cavity when activation is desired. The activation source 46 can comprise a source of heat. Alternatively, the activation source 46 can comprise an electrical field source to resistively heat the structure, or a mechanical energy source. Alternatively, magnetic alloys could be used that heat up when exposed to an external alternating magnetic field. As FIG. 10A shows, the relatively compliant mechanical properties of the structure return when the structure 12 is cooled sufficiently to return to the soft martensitic phase. For example, the individual could drink a sufficiently cool or cold liquid, or use the wand 50 set at a sufficiently cool temperature to return the structure to a relatively compliant condition.

b. Shape Memory Ferromagnetic Alloys

An implanted kinetic structure 12 can comprise a shape memory ferromagnetic alloy 52 that assumes a predetermined, remembered shape in response to a magnetic field 54. The alloy 52 can comprise, e.g., Ni—Mn—Ga alloys close to the stoichiometric composition $Ni_2MnGa$.

Shape memory ferromagnetic kinetic structures 12 are well suited for implantation in the tongue, the vallecula, the soft palate, or a pharyngeal wall, as well as other targeted pharyngeal structures and other anatomic components within the pharyngeal conduit. FIG. 11A shows an implanted kinetic structure 12 made of a shape memory ferromagnetic memory alloy 52 implanted, for the purposes of illustration, in the base of the tongue. As FIG. 11A shows, the structure 12 possesses relatively compliant mechanical properties in the absence of an external magnetic field 54. In response to exposure to an external magnetic field 54 (see FIG. 11B), the structure 12 assumes less compliant mechanical properties, accompanied by pronounced shape change. In this phase, the structure 12 provides a stiffening resistance to shape change. In the illustrated embodiment, the external magnetic field 54 is brought about permanent magnets or an electromagnet worn by the individual, e.g., carried by a collar 48 secured about the neck of the individual, in the manner shown in FIG. 10C. The source of the magnetic field 54 can also be carried on a wand 50 in the manner shown in FIG. 10D. In the absence of the external magnetic field 54 (as FIG. 11A shows), the relatively compliant mechanical properties of the structure 12 return.

2. Selective Magnetic Activation

Figure 12A:
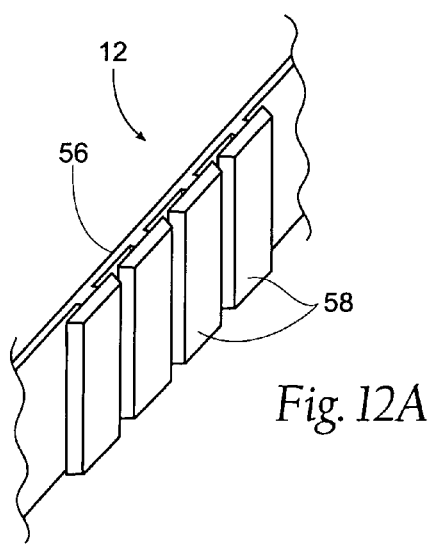
FIGS. 12A to 12E show an implanted kinetic force structure of a type shown in FIG. 2A that includes an array of soft ferromagnetic materials that, when magnetized, assumes a predetermined shape.
Figure 12B:
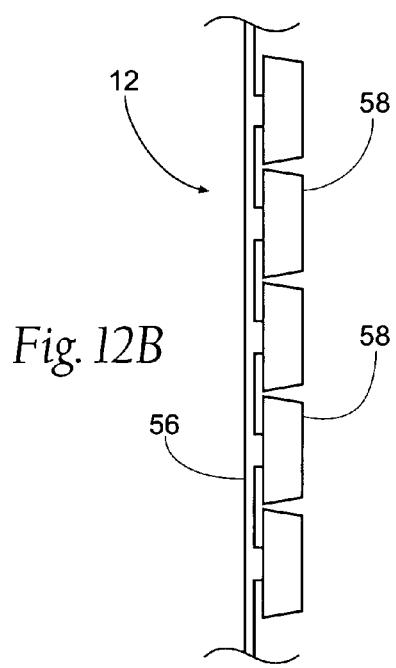

As FIGS. 12A and 12B show, an implanted kinetic structure 12 can comprise an array of soft ferromagnetic materials 58 mounted on a flexible carrier 56. A soft ferromagnetic material 58 is a material that can be demagnetized very easily, once having been magnetized. In other words, a soft ferromagnetic material 58 retains almost no residual magnetism after the magnetizing force is removed. Soft ferromagnetic materials 58 have very high permeability and saturation magnetization, but very low intrinsic coercivity. Soft magnetic materials 58 can be attracted by a permanent magnet or an electromagnet.

Examples of known soft ferromagnetic materials 58 include Iron (Fe); Nickel (Ni); Permendur; MuMetal, low-carbon steels, Iron-Cobalt alloys (Fe—Co); silicon steels; and amorphous alloys.

The soft ferromagnetic materials 58 can be machined, laser cut, chemically etched, or EDM manufactured into magnetic blocks and encased, packaged, or otherwise arranged on the flexible carrier 56 to form a magnetic array structure 12, as FIGS. 12A and 12B show. In the absence of a magnetic force 60, the array structure 12 possesses compliant mechanical properties.

Figure 10C:
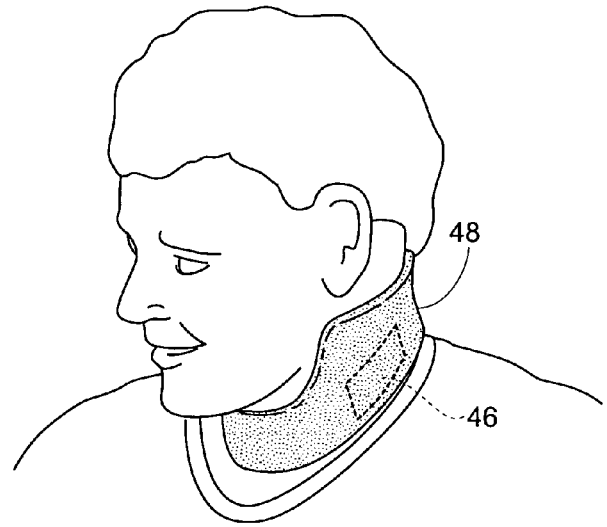
Figure 10D:
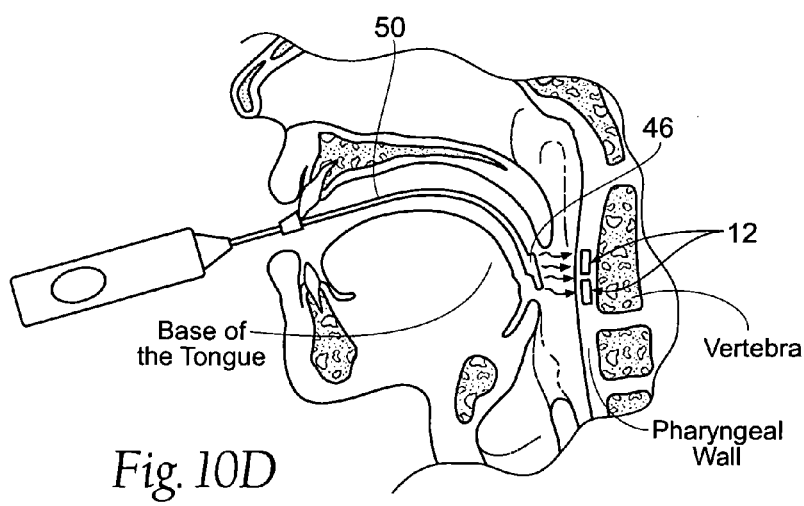
Figure 11A:
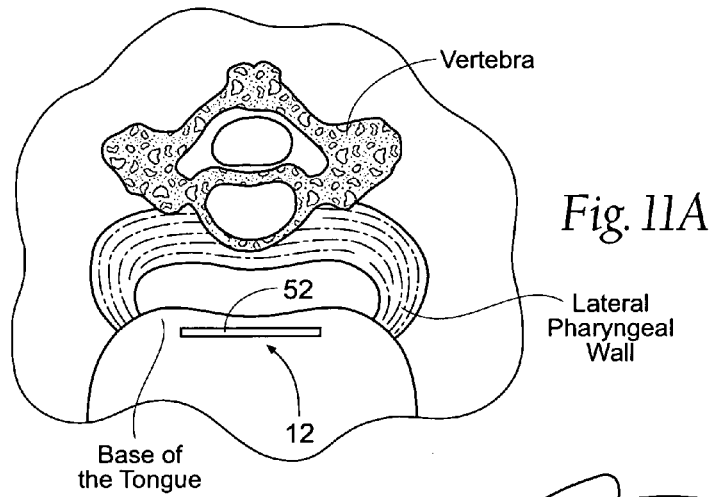
FIGS. 11A and 11B show an implanted kinetic force structure of a type shown in FIG. 2A that includes a shape-memory ferromagnetic alloy that assumes a predetermined shape in response to an applied magnetic field, FIG. 11A showing the structure before shape activation, and FIG. 11B showing the structure after shape activation.
Figure 11B:
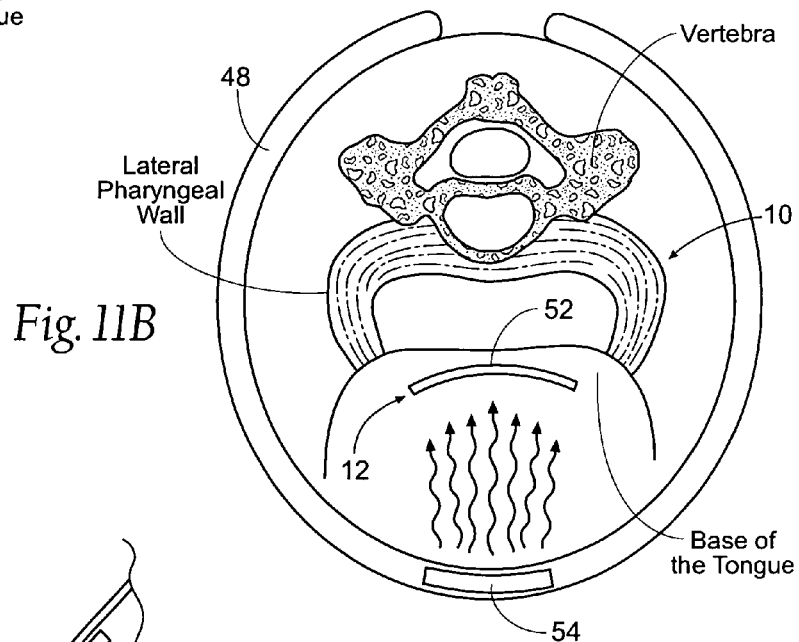
Figure 12C:
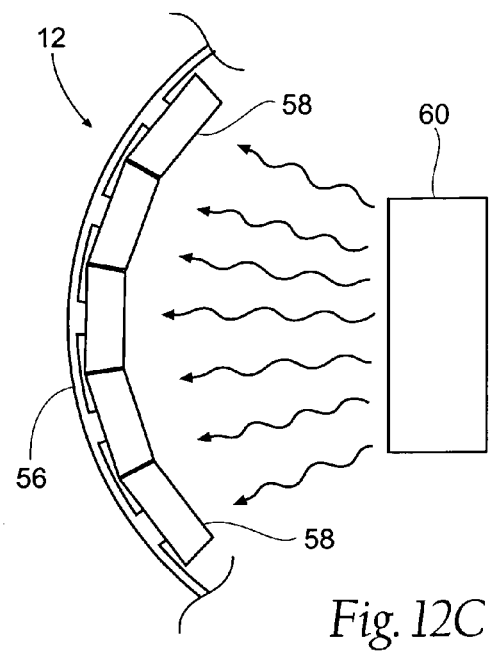

In this arrangement (see FIG. 12C), when activation of the soft ferromagnetic array structure 12 is desired, an external source of magnetic force 60 (which can comprise, e.g., a second array with permanent magnets, or a single permanent magnet, or an electromagnet) can be donned by the individual (e.g., in the collar 48 shown in FIG. 10C or wand 50 shown in FIG. 10D). Exposure of the soft ferromagnetic array structure 12 to the source of magnetism 60 causes the array to become magnetic. The external magnetic force 60 is sized and configured to make adjacent surfaces of soft magnetic blocks 58 have unlike poles, and are thereby attracted to one another. This attraction will case the carrier 56 to bend (as FIG. 12C shows), until the magnetic blocks 58 come into contact with each other. This attraction and contact will be maintained until the source of magnetism 60 is removed or reduced in intensity. This continuous, dynamic magnetic force will resists straightening of the carrier 56. This dynamic, magnetically induced resistance to shape change, in turn, exerts a dynamic force on neighboring tissue, to impart a desired new morphology and/or motility and/or shape to the tissue, together with a corresponding resistance to change in this condition, to achieve the desired physiologic response. Selectively magnetically shaped structures 12 are well suited for implantation in the tongue, vallecula, soft palate, a pharyngeal wall, as well as in other targeted pharyngeal structures and other anatomic components within the pharyngeal conduit. FIG. 12E shows a magnetically shaped structure 12 of the type shown in FIGS. 12A and 12B implanted, for the purpose of illustration, in the soft palate. Exposure of the structure 12 to a source of magnetism 60 bends the structure 12 in the manner shown in FIG. 12C, pulling the soft palate forward.

Figure 12D:
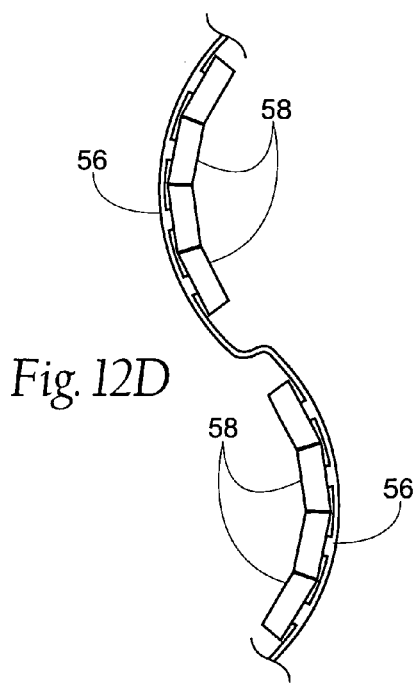
Figure 12E:
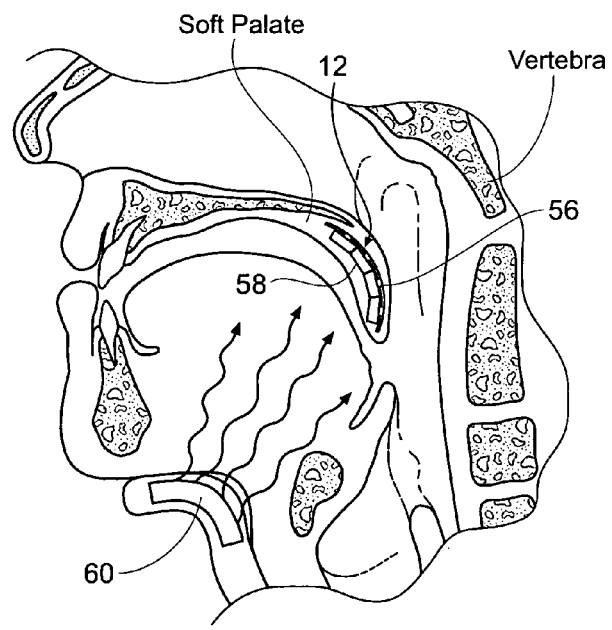

As FIG. 12D shows, the soft ferromagnetic material 58 can be mounted to the carrier 56 to cause serpentine bending. Serpentine bending can be achieved by affixing similar ferrous blocks 58 on the opposite surface of the flexible carrier 56, displaced axially from the blocks on the first surface. The flexible carrier 58 may be produced with an offset between the two areas if it is desirable to maintain a thin overall thickness of the assembly.

IV. Biocompatibility

Figure 13:
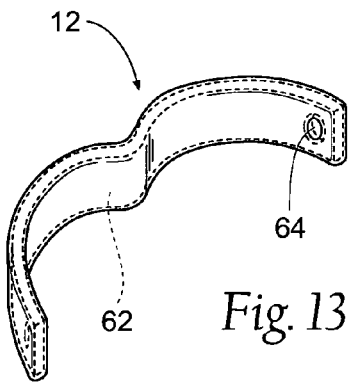
FIG. 13 show an implanted static and/or kinetic force structure of a type shown in FIG. 2A that carries a protective material.

As FIG. 13 shows, a given implanted static or kinetic structure 12 of whatever form or configuration can be coated, plated, encapsulated, or deposited with a selected protective material 62. The protective material 62 is selected to provide a corrosion resistant and biocompatible interface, to prevent interaction between the structure and tissues/fluids of the body. The protective material 62 is also desirably selected to form a durable tissue interface, to provide longevity to the structure, and thereby provide resistance to structural fatigue and/or failure. The protective material 62 can be selected among various types of materials known to provide the desired biocompatibility, resistance to corrosion, and durability. For example, the protective material 62 can comprise gold and/or titanium material plated, deposited, or otherwise coated upon the structure. As another example, the protective material 62 can comprise a parylene coating. As other examples, the protective material 62 can comprise a silicone polymer, a non-toxic epoxy, a medical grade polyurethane, or a U.V. curable medical acrylic co-polymer.

The protective material 62 may also incorporate anticoagulants and/or antibiotics.

V. Fixation of Static or Kinetic Implants

A. Use of Mechanical Fixation Materials

The position of implanted structures 12 can be fixed against migration in a targeted tissue region within the pharyngeal conduit using conventional mechanical fixation materials and techniques known in the surgical arts, e.g., non-resorbable sutures, screws, staples, adhesives, or cements such as polymethyl methacrylate (PMMA) cement. For example, the structures 12 can include preformed apertures 64 to accommodate the fixation material, i.e., sutures, screws or staples. Fixation to tissue enhances the fixation or bracing function of the implanted static or kinetic structure.

The tissue to which a given implant is fixed can include soft tissue in the pharyngeal walls, the base of the tongue; the vallecula; the soft palate with uvula; the palatine tonsils with associated pillar tissue, and the epiglottis.

The tissue can also include bone within the pharyngeal conduit, e.g., a hyoid bone or a vertebra, as will be next described.

B. Fixation to a Vertebra

Figure 14A:
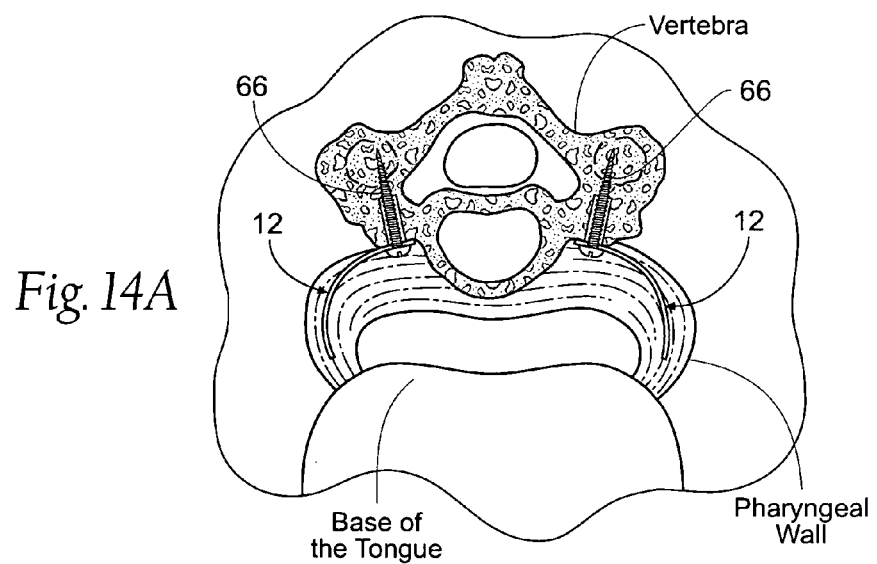
FIGS. 14A and 14B show an implanted static and/or kinetic force structure of a type shown in FIG. 2A that is fixed to a vertebra.
Figure 14B:
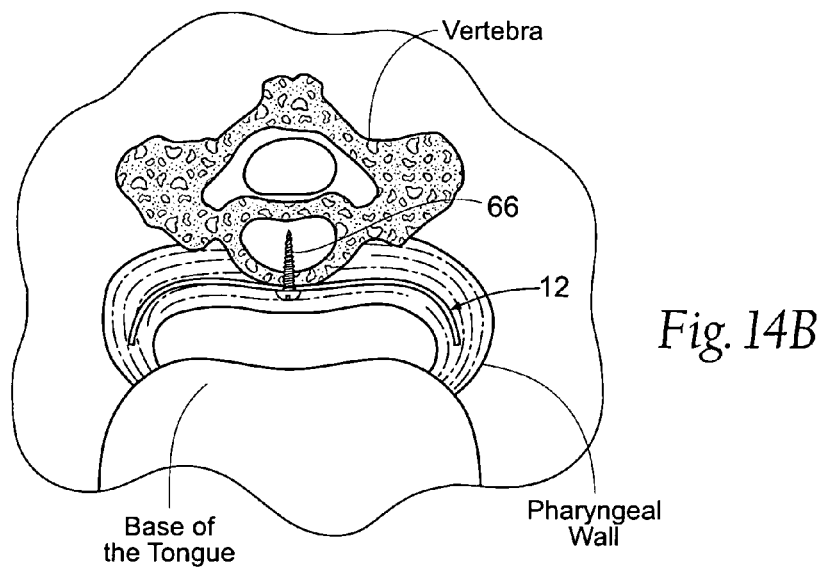

In some cases, implantation of one or more structures 12, with fixation to bone, may be desirable. As FIG. 14A shows, one or more given implanted static or kinetic structures 12 may be fixed to one or more vertebrae with fixation elements 66 such as bone screws and/or adhesives and/or bone cements. As FIG. 20A also shows, such structures 12 can be fixed, e.g., at or near the pedicles. Alternatively (as FIG. 14B shows), one or more implanted static or kinetic structures 12 may be fixed with a fixation element 66 such as a bone screw to other regions of the vertebra. A single fixation point may be used to secure multiple implanted static or kinetic structures.

Figure 20A:
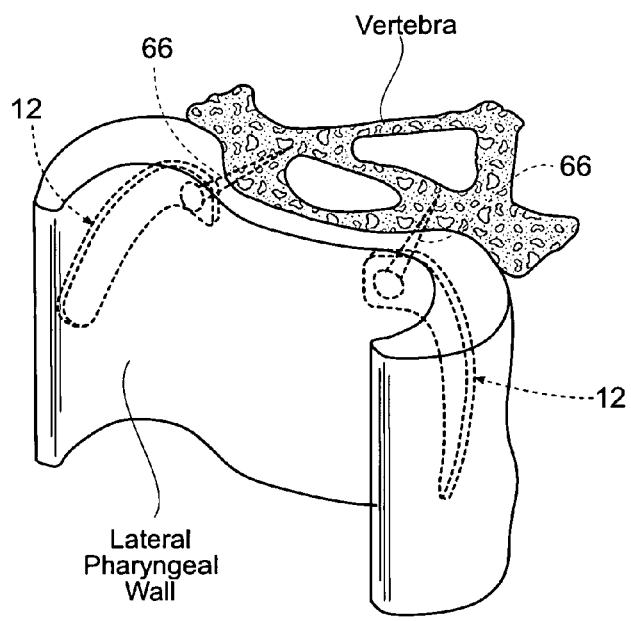
FIGS. 20A and 20B show an implanted static and/or kinetic force structure of a type shown in FIG. 2A that is fixed to a vertebra.
Figure 20B:
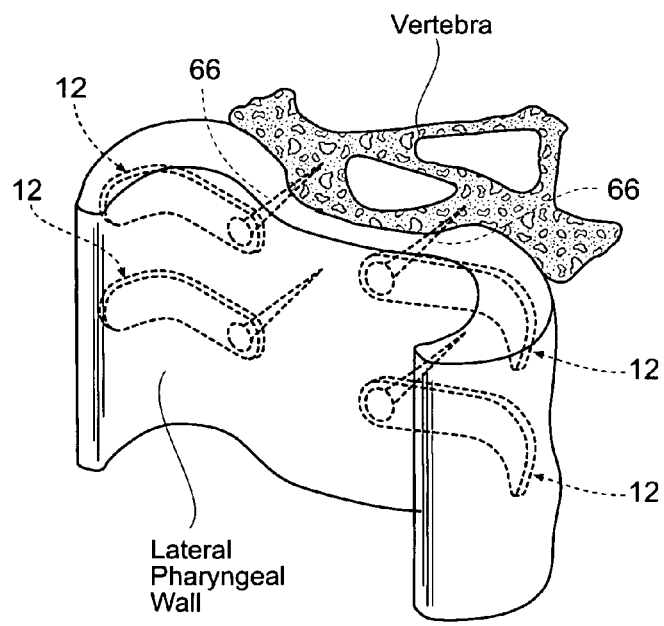

With vertebra fixation, several static or kinetic structures 12 may be oriented horizontally in a single row or in a fan or in a vertically stacked relationship along the pharyngeal conduit (as shown in FIG. 20B), in an angular path within a lateral pharyngeal wall (as shown in FIG. 20A).

In this way, fixation or bracing of the lateral pharyngeal wall can be achieved by using implanted static or kinetic structure or structures 12 that are stabilized with a vertebral column bone anchor. Fastening to bone enhances the fixation or bracing function of the implanted static or kinetic structure 12.

Figure 24A:
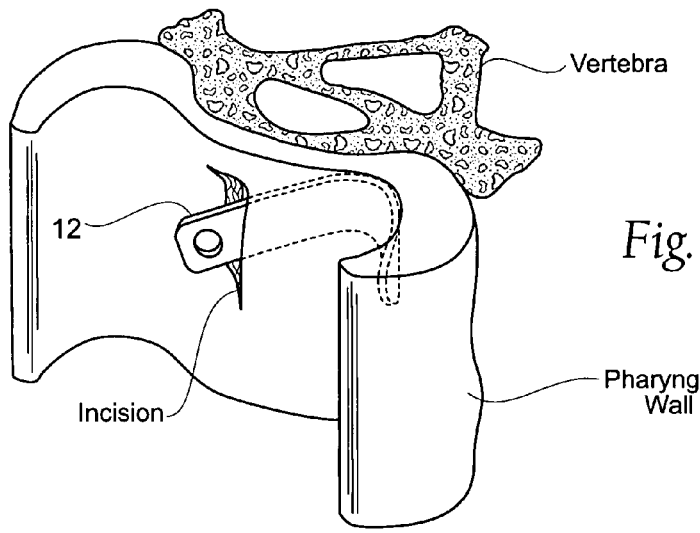
FIGS. 24A to 24C show an illustrative surgical procedure for the implantation of a static and/or kinetic structure of the type shown in FIGS. 14A and 14B and FIGS. 19A and 19B, during which the structure is fixed to a vertebra.
Figure 24B:
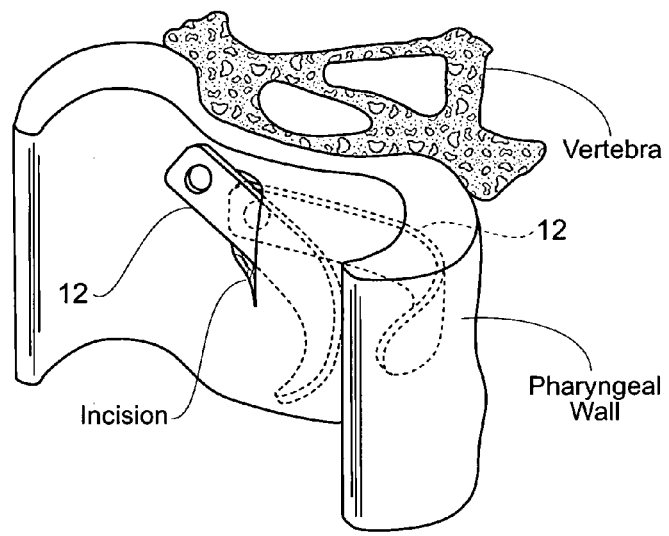
Figure 24C:
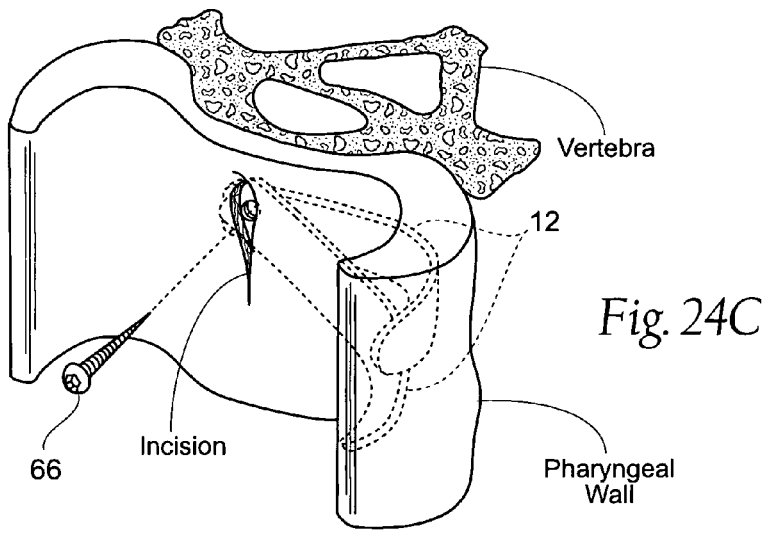

In representative procedure for implanting a pharyngeal wall implant 12 or other pharyngeal wall device that is fixed to a vertebral body (see FIGS. 24A to 24C): (1) a patient is positioned in the Rose tonsillectomy position (supine, head extended), and with the pharynx exposed using a Crowe Davis, or similar tonsillectomy mouth retractor; (2) the anterior aspect of the cervical vertebra is identified along the posterior pharyngeal wall; (3) a small transverse incision (see FIG. 24A) is made just lateral to midline, and deepened to the body of a cervical vertebra, exposing bone; (4) the implant 12 can be inserted through this incision (as FIG. 24A shows) and tunneled submucosally along the lateral pharyngeal wall, using manual palpation along the mucosa for guidance; (5) when proper placement is established, the implant 12 is released; (6) a new implant 12 (see FIG. 24B) is then loaded through the same small incision, angling the placement downward. In this fashion, an array of implants 12 can be placed within the submucosal space along the pharyngeal wall. The proximal ends of all the implants 12 placed are configured with a rounded ring (like a flat washer). All of these rings are then placed on the shaft of a self tapping screw (see FIG. 24C) which is then secured to the vertebral column as the bone anchor. The area is irrigated with antibacterial solution and the small incision is closed in two layers (periosteum, then mucosa). An identical procedure is then carried out on the contralateral pharyngeal side, establishing two separate sets of arrayed submucosal wall implants.

C. Tissue In-Growth Surfaces

In addition to any of the just-described tissue fixation methodologies, the implanted static or kinetic structure can include a tissue in-growth surface 68 (see FIG. 15). The surface 68 provides an environment that encourages the in-growth of neighboring tissue on the implanted structure. Tissue in-growth is defined as the filing of pores in an implanted material with cellular material. As in-growth occurs, the implanted structure 12 will become securely anchored, resisting migration or extrusion from the tissue. The tissue in-growth surface 68 thus enhances tissue adhesion and stabilization, and thereby further stabilizes and fixes the position of the implanted structure 12 in the targeted implantation site.

The tissue in-growth surface 68 can be formed in various ways. For example, the surface can comprise an open cellular or fibrous structure, biologically inert in nature and known to support in-growth by body tissue. One material that exhibits this characteristic is expanded PTFE (polytetrafluoroethylene or Teflon®-DuPont). This material may be prepared by radiation bombardment to cause the structure of the material to become fractured and fibrous in nature. The resulting material is open and porous, providing fissures into which fluids may enter and to which body tissue can attach and grow. Other such inert polymers and even metals (such as nickel titanium—Nitinol®) when treated or coated to provide a granular or fibrous surface, may offer a substrate for tissue in-growth. An alternative form of the in-growth matrix may be an open celled polymeric foam (e.g., PVA foam) in place of a material that must be irradiated to attain the open fibrous or granular nature.

The in-growth surface 68 can also comprise, e.g., woven or knitted Dacron® (PET) fabric placed on a substrate of polydimethylsiloxane (PDMS) or polyurethane (PU); metallic surface structures created by electroform processing; a sintered metal surface (e.g., stainless steel, platinum, iridium, or alloys thereof); parylene coatings; or diffusion limited aggregated silicones. The in-growth surface can also comprise mechanical structures, such as spike, staples, times, coils, or perforations of appropriate dimensions associated with the implant. The implant may also include compounds to promote coagulation and/or antibiotics to prevent infection, used alone or in combination with the in-growth surface 68.

It may be desirable to mechanically anchor the implant 12 while allowing in-growth to occur. Temporary anchoring may be accomplished by use of resorbable sutures, screws or other mechanical fasteners made of resorbable materials such as polyglycolic acid or other similar compounds. Tissue adhesives and/or tissue cements such as PMMA may also be used to provide tissue adhesion, fixation, and stabilization.

Complete tissue in-growth is determined by the percentage of the material that has been infiltrated by the cellular material. With pore sizes from 100 micrometers to 500 micrometers, blood vessels can be formed. With pore sizes of 10 micrometers to 100 micrometers, cells to small capillaries can form.

VI. Orienting Implanted Static or Kinetic Structures

The orientation of the static or kinetic structures can vary according to the particular anatomy of the targeted tissue region and its environs.

A. Horizontal Orientation

For example, the particular anatomy and tissue mass of the targeted tissue region may lend itself to the implantation of the static or kinetic structures 12 in a generally horizontal plane. With respect to anatomic landmarks, horizontal arrays extend either laterally (from side to side) or anterior-to-posterior (front to back), following the natural morphology of the tissue.

For example (see FIG. 16A), the anatomy and the tissue mass of the tongue accommodates implantation of a horizontal array of static or kinetic structures 12, either laterally in the base of the tongue, or anterior-to-posterior along one or both sides of the tongue, or both. As FIG. 16B shows, horizontal arrays of static or kinetic structures 12 can be implanted in stacked or staggered fashion on the posterior of the tongue, at different elevations along the pharyngeal conduit.

As another example (see FIG. 17A), the anatomy and the tissue mass of the lateral pharyngeal wall accommodates implantation of a horizontal array of multiple static or kinetic structures 12 following the morphology of the posterior and lateral pharyngeal walls. In the pharyngeal wall (see FIG. 17B), one or more shaped static or kinetic structures 12 can remodel tissue along a substantial portion of the airway, from the spinal column to the base of the tongue.

As FIG. 17C shows, horizontal arrays of multiple static or kinetic structures 12 can be implanted in stacked or staggered fashion within the lateral pharyngeal wall. The structures may be discontinuous or form concentric bands about the pharyngeal wall at different elevations along the pharyngeal conduit.

B. Vertical Orientation

The particular anatomy and tissue mass of the targeted tissue region may lend itself to the implantation of multiple static or kinetic structures 12 in a generally vertical plane. With respect to anatomic landmarks, vertical arrays extend in a superior (cephalad)-to-inferior (caudal) direction, following the natural morphology of the tissue mass.

Figure 18A:
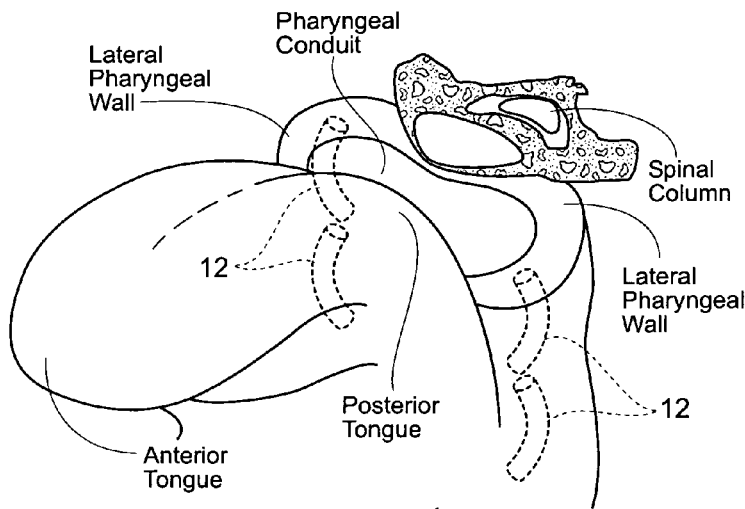
FIGS. 18A to 18C show static and/or kinetic force structures of a type shown in FIG. 2A implanted in vertical arrays in targeted pharyngeal structures and individual anatomic components within the pharyngeal conduit.

For example (see FIG. 18A), the anatomy and the tissue mass of the pharyngeal wall accommodates implantation of a vertical array of multiple static or kinetic structures 12 following the morphology of opposite lateral pharyngeal walls.

Figure 18B:
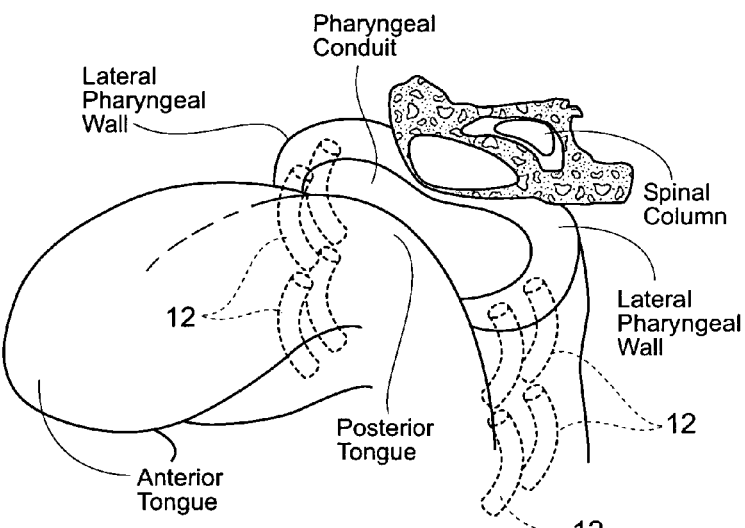

As FIG. 18B shows, vertical arrays of multiple static or kinetic structures 12 can be implanted either end-to-end or side-by side within the lateral pharyngeal wall.

Figure 18C:
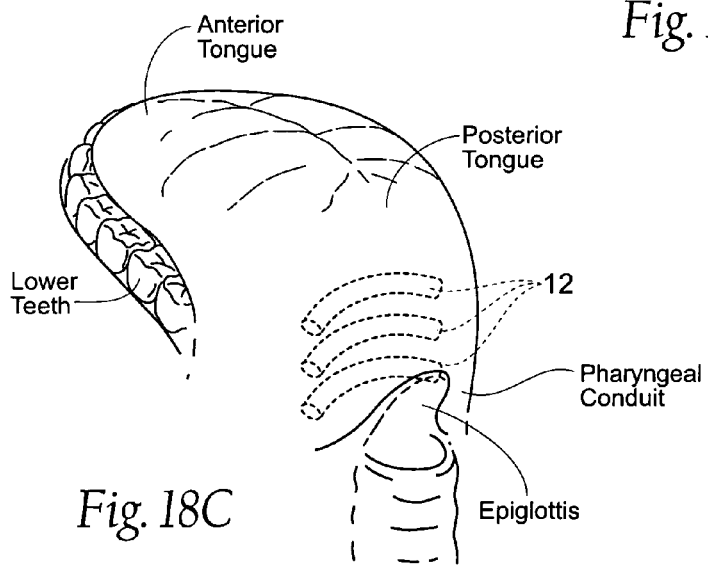

As FIG. 18C shows, the anatomy and the tissue mass of the base of the tongue and the vallecula accommodate implantation of a vertical array of multiple static or kinetic structures 12 following the morphology of these anatomic components within the pharyngeal conduit.

C. Other Orientations

The particular anatomy and tissue mass of the targeted tissue region may lend itself to the implantation of multiple static or kinetic structures 12 in both a generally horizontal plane and a generally vertical plane.

Figure 19A:
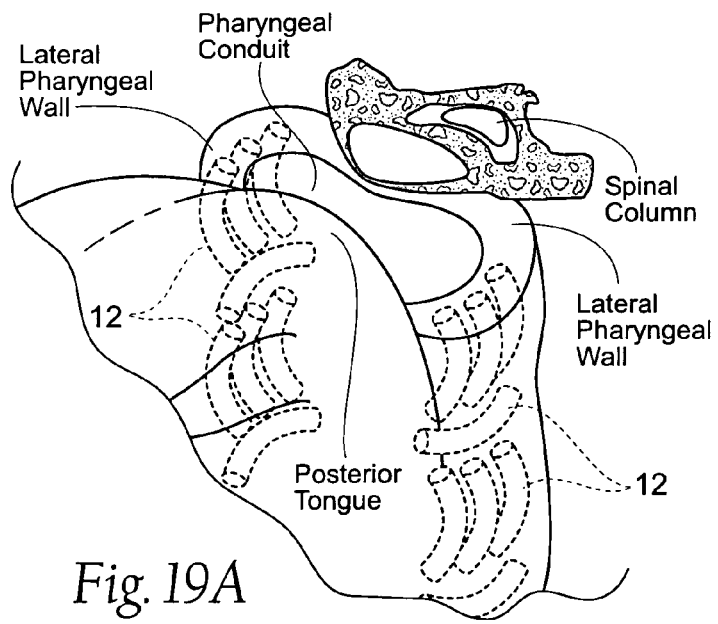
FIGS. 19A and 19B show static and/or kinetic force structures of a type shown in FIG. 2A implanted in mixed vertical and horizontal arrays and in mixed non-horizontal and non-vertical arrays in targeted pharyngeal structures and individual anatomic components within the pharyngeal conduit, with fixation to a vertebra.

For example (see FIG. 19A), the anatomy and the tissue mass of the pharyngeal wall accommodates implantation of vertical arrays of multiple static or kinetic structures 12 with horizontal arrays of static or kinetic structures 12 along the elevation of the pharyngeal conduit. This implantation pattern makes possible the formation of dynamic bracing or fixation forces that facilitate the physiologic objective of resisting tissue collapse along the pharyngeal conduit.

The particular anatomy and tissue mass of the targeted tissue region may lend itself to the implantation of multiple static or kinetic structures 12 in angular planes (i.e., not horizontal or not vertical planes).

Figure 19B:
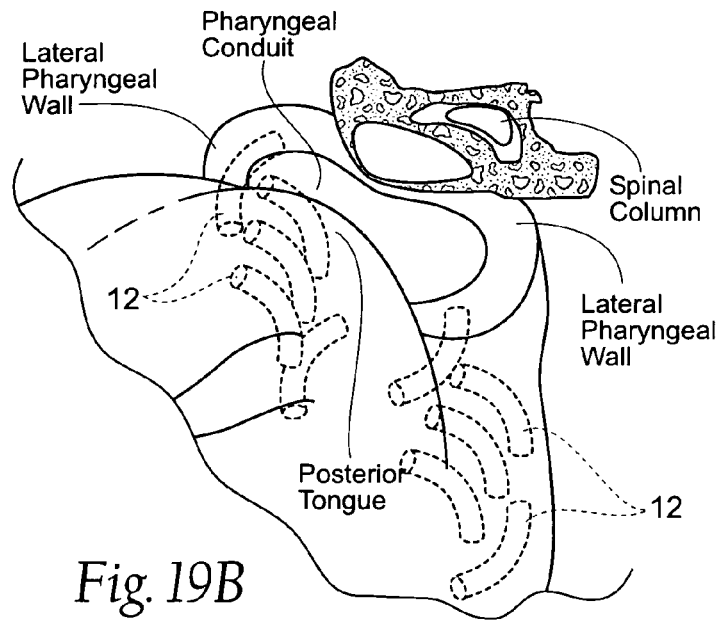

For example (see FIG. 19B), the anatomy and the tissue mass of the pharyngeal wall accommodates implantation of angular, non-horizontal and non-vertical arrays of multiple static or kinetic structures 12. This complex implantation pattern makes possible the formation of dynamic bracing or fixation forces that facilitate the physiologic objective of resisting tissue collapse along the pharyngeal conduit.

VII. Illustrative Implanted Force Systems

Based upon the foregoing discussions, a practitioner can select and assemble static and/or kinetic structures 12 in various ways to create systems 10 of different configurations to achieve the desired physiologic response. The static and/or kinetic structures 12 are well suited for implantation within the pharyngeal walls (with or without fixation to a vertebral body); the base of the tongue; the vallecula; and the soft palate/uvula. Representative examples of embodiments of magnetic force systems 10 in certain targeted pharyngeal structures and individual anatomic components within the pharyngeal conduit will be described in greater detail now.

A. Implants Within the Pharyngeal Wall and Adjacent Structures

Figure 21:
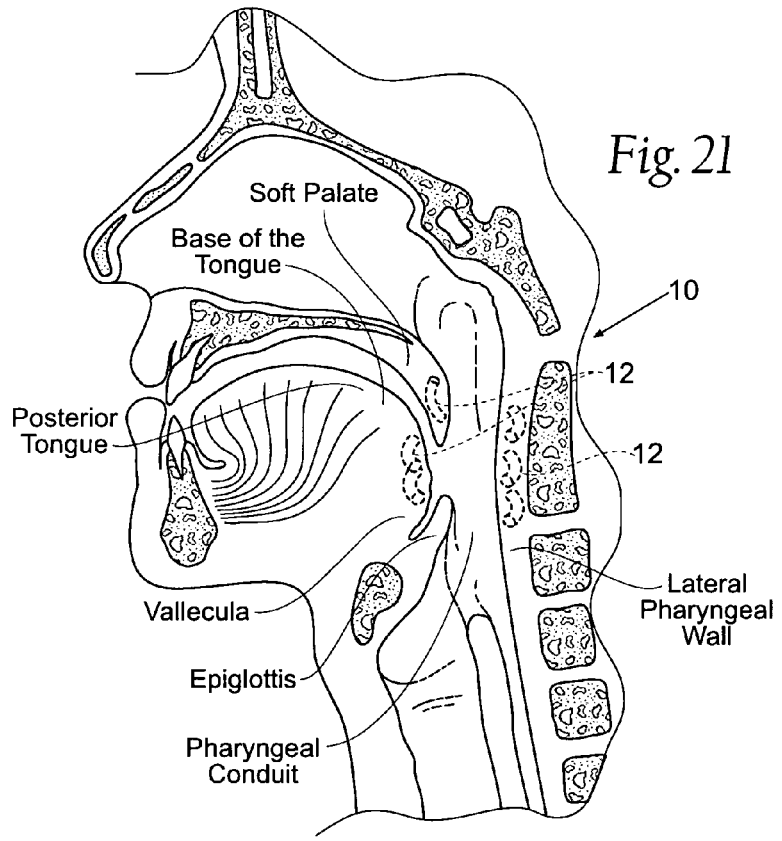
FIG. 21 shows an illustrative embodiment of a system of the type shown in FIG. 2A that includes static and/or kinetic force structures implanted in the pharyngeal wall and adjacent anatomic structures such as the tongue, vallecula, and soft palate.

FIG. 21 shows an illustrative embodiment of a system 10 that includes static and/or kinetic structures 12 that are implanted in a vertical arrays on opposite lateral sides of the pharyngeal wall (with or without fixation to a vertebral body), the base of the tongue, the vallecula, and the soft palate/uvula. The structures 12 can be selected among the various static and kinetic types previously discussed. It should be appreciated that stacked horizontal arrays, or a combination of horizontal and vertical arrays, or angular arrays could be used. Each structure remodels tissue in its vicinity, providing bracing or fixation forces that facilitate the physiologic objective of resisting tissue collapse along the pharyngeal conduit, when imminent. It should be appreciated that static and/or kinetic structures 12 need not be implanted precisely in the manner shown or at every anatomic site shown to achieve the desired physiologic objective.

B. Implants Within the Tongue and Adjacent Structures

Figure 22A:
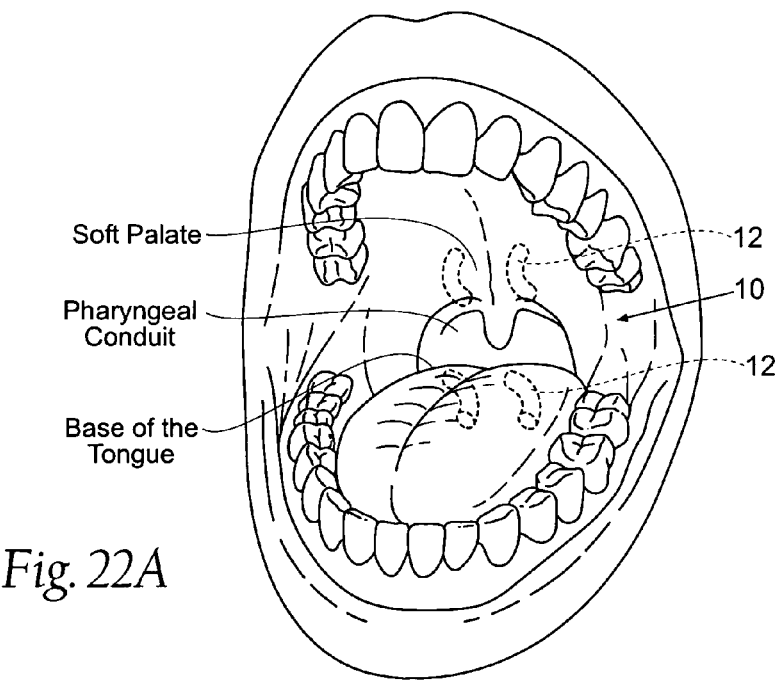

FIG. 22A shows another illustrative embodiment of a system 10 that includes static and/or kinetic structures 12 that are implanted on opposite lateral sides in the base of tongue as well as in the soft palate. The structures 12 can be selected among the various static and kinetic types previously discussed. It should be appreciated that other arrays, or a combination of arrays arrays could be used. Each structure 12 remodels tissue in its vicinity, providing bracing or fixation forces that facilitate the physiologic objective of resisting tissue collapse along the pharyngeal conduit. It should be appreciated that static and/or kinetic structures 12 need not be implanted precisely in the manner shown or at every anatomic site shown to achieve the desired physiologic objective.

FIGS. 22B and 22C show another illustrative embodiment of a system 10 that includes one or more selectively kinetic structures 12 that are implanted across the base of the tongue. In FIG. 22B, the implanted structure 12 is shown in a non-activated configuration. In FIG. 22C, the selectively kinetic structure 12 is subject to a suitable activation force (as previously described), causing the implanted structure to assume a desired activated configuration. In this configuration, the implanted structure remodels the base of the tongue. The configuration shown in FIG. 22C includes a depression 70 in the middle of the tongue base, which resists closure of the airway during sleep, and a prominence 72 on the right and left lateral sides of the tongue base, which serve to press against the lateral oropharyngeal tissue, holding the tongue in an anterior position.

FIGS. 22D and 22E show another illustrative embodiment of a system 10 that includes one or more selectively kinetic structures 12 that are implanted in the posterior of the tongue and vallecula. In FIG. 22D, the implanted structures 12 are shown in a non-activated configuration, extending horizontally along the posterior of the tongue and the vallecula. In FIG. 22E, the selectively kinetic structures 12 are subject to a suitable activation force (as previously described), causing the implanted structures to assume a desired activated configuration. In this configuration shown in FIG. 22E, the implanted structures remodel the posterior of the tongue and vallecula, creating a depression 70 that runs vertically down the posterior surface of the tongue and the vallecula.

VIII. Illustrative Structures Useable with the Pressure Chamber System

Figure 23A:
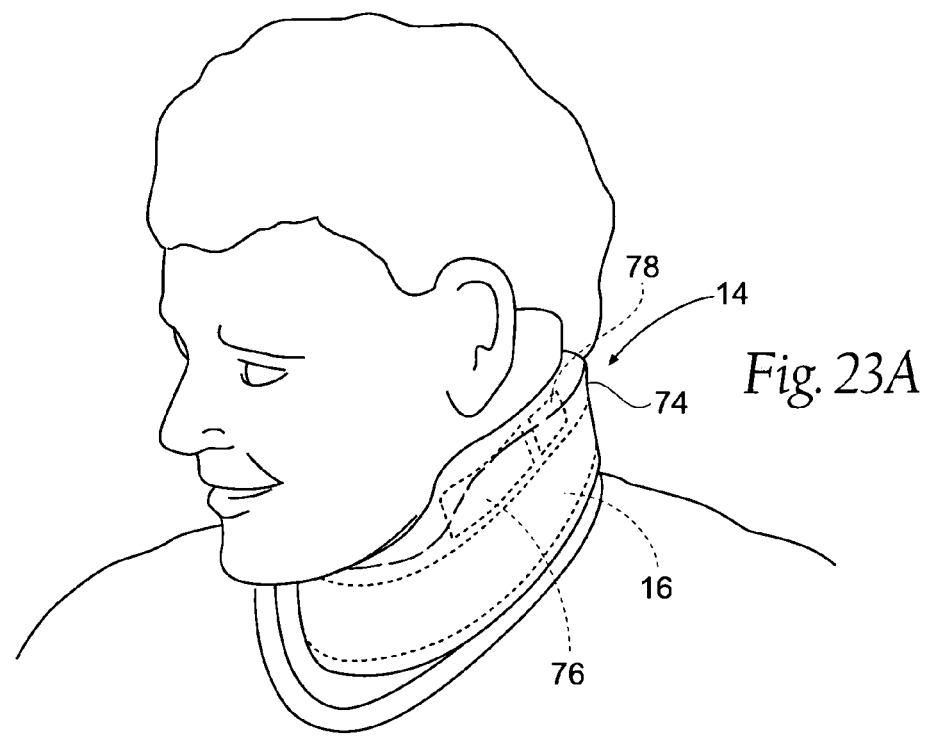
FIGS. 23A and 23B show a pressure chamber system of a type shown in FIG. 2B.
Figure 23B:
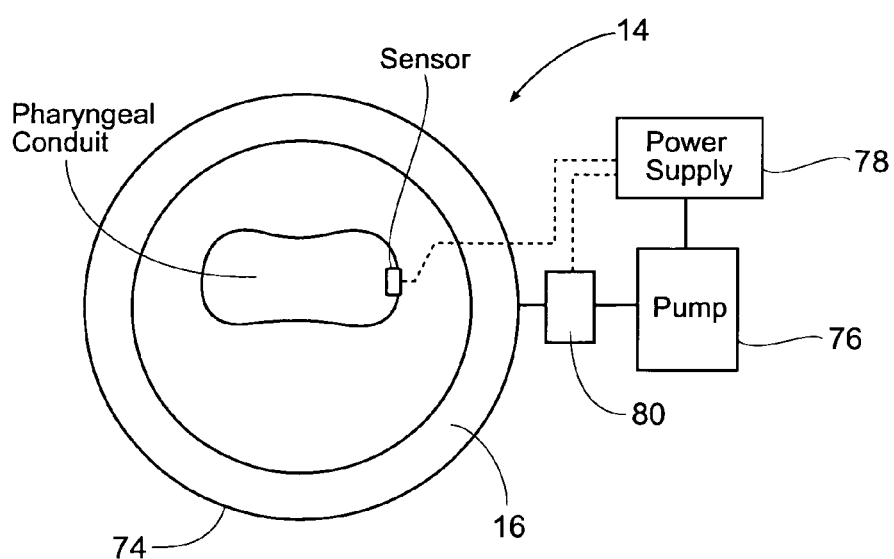

FIGS. 23A and 23B show an illustrative embodiment of a pressure chamber system 14. The system 14 includes a collar 74 that is sized and configured to be removably worn about the neck of an individual when the desired physiologic effect is desired, e.g., during sleep (as FIG. 23A shows).

The collar 74 carries a pressure-retaining chamber 16. When the collar 74 is worn, the chamber 16 encircles all or a portion of the pharyngeal conduit (see FIG. 23B). The chamber 16 may comprise an elastic material for comfort.

An air pump 76 has an inlet that communicates with the chamber 16 and an outlet that communicates with the ambient environment. The air pump 76 can be carried by the collar 74 (as shown), or it can be located remote from the collar, e.g., bedside, and coupled by tubing to the air chamber 16. The air pump 76 can comprise, e.g., a diaphragm pumping mechanism, or a reciprocating piston mechanism, or a centrifugal (turbine) air-moving mechanism.

The air pump 76 may be manually operated, or a power source 78 may drive the air pump 76. The power source 78 can be, e.g., an electric motor that can be plugged into a conventional electrical receptacle, or be battery-powered, or both (in which case the battery can be rechargeable). When driven, the air pump 76 draws air from the chamber 16, to establish within the chamber 16 a pressure condition that is less than atmospheric.

A regulator 80 may be coupled to govern operation of the air pump 76 to establish and maintain a desired sub-atmospheric pressure condition within the chamber 16. The desired pressure condition is selected to be less than atmospheric pressure and is desirably less the minimum pressure condition expected experienced in the pharyngeal conduit, which is typically encountered during the inhalation phase of the respiration cycle. The pressure selected desirably nullifies the vector sum of the extralumenal forces, which are created by the interaction of atmospheric pressure, gravity, the contractive forces within the tissue due to upper airway muscle activity, and the inward forces generated by subatmospheric luminal pressure generated during inhalation. It is believed that the pressure condition established within the chamber 16 should be at least $-1$ cm $H_2O$ and desirable at least $-10$ $H_2O$. The pressure created by the system 14 desirably also takes into account different anatomical structural differences of individual airways.

The system 14 can also include some form of physiologic feedback control for the air pump. In this arrangement, the system includes a monitor or sensor 82 to sense fluctuations of pharyngeal pressure during the respiration cycle. When the pharyngeal pressure meets or exceeds a selected threshold minimum pressure, the monitor 82 sends a control signal to the pump 76, to activate the pump 76. The pump 76, when activated, operates to maintain a desired pressure condition within the chamber 16 while sensed pharyngeal pressure is below the threshold. The pump 76, when activated, could also operate to maintain a desired pressured differential between pressure in the chamber 16 and the sensed pharyngeal pressure while sensed pharyngeal pressure is below the threshold. Once pharyngeal pressure exceeds the threshold, the monitor 82 sends a control signal to deactivate the pump 76. In this way, the system 14 conditions tissue to resist collapse when respiratory conditions are most conducive to collapse, but otherwise does not affect the tissue morphology and/or motility and/or shape. The pressure chamber 16 can also serve to reduce tissue vibration and be used in the treatment of snoring.

Other forms of physiologic feedback control can be used. For example, airflow can be measured during the respiratory cycle, and/or the expansion/contraction of the chest can be monitored during the cycle. Chamber pressure can be varied to response to requirements dictated by the respiratory cycle.

The above-described embodiments of this invention are merely descriptive of its principles and are not to be limited. The scope of this invention instead shall be determined from the scope of the following claims, including their equivalents.

What is claimed is:

1. A method for fixating targeted pharyngeal tissue in the wall of a pharyngeal conduit, the method comprising:
    forming a generally elongate tissue space within the targeted pharyngeal tissue; and
    forming a non-liquid, static mechanical implant structure within the tissue space by injecting a biocompatible liquid into the tissue space in the targeted tissue, wherein the tissue space is sized and shaped such that the resulting implant structure brings about a desired physiologic response in the targeted pharyngeal tissue.

2. The method of claim 1, wherein the biocompatible liquid contains solid particles.

3. The method of claim 2, wherein the particles are magnetic.

4. The method of claim 2, wherein the particles are ferrous.

5. The method of claim 1, wherein the tissue space is formed using a trocar.

6. The method of claim 1 wherein at least a portion of the injected biocompatible liquid cross-links, polymerizes, or otherwise chemically reacts to form at least a portion of the non-liquid, static mechanical implant structure.

7. A method for implanting an apparatus in a tissue, the method comprising:
    providing at least one liquid;
    implanting a sealed container into a tissue, the sealed container being preshaped prior to implanting; and
    injecting the liquid into the sealed container.

8. The method of claim 7, wherein the sealed container is expandable.

9. The method of claim 7, wherein the sealed container is bioresorbable.

10. The method of claim 7, wherein the sealed container is placed in a void within the tissue.

11. The method of claim 10, wherein the void is created by dilation of the tissue.

12. The method of claim 7, wherein the liquid contains solid particles.

\* \* \* \* \*